US 12,259,272 B2

(12) United States Patent
Ashry et al.

(10) Patent No.: US 12,259,272 B2
(45) Date of Patent: Mar. 25, 2025

(54) RED PALM WEEVIL DETECTION BY APPLYING MACHINE LEARNING TO SIGNALS DETECTED WITH FIBER OPTIC DISTRIBUTED ACOUSTIC SENSING

(71) Applicant: KING ABDULLAH UNIVERSITY OF SCIENCE AND TECHNOLOGY, Thuwal (SA)

(72) Inventors: Islam Ashry, Thuwal (SA); Boon Siew Ooi, Thuwal (SA); Yuan Mao, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 273 days.

(21) Appl. No.: 17/913,003

(22) PCT Filed: Mar. 9, 2021

(86) PCT No.: PCT/IB2021/051951
§ 371 (c)(1),
(2) Date: Sep. 20, 2022

(87) PCT Pub. No.: WO2021/191714
PCT Pub. Date: Sep. 30, 2021

(65) Prior Publication Data
US 2023/0160743 A1 May 25, 2023

Related U.S. Application Data

(60) Provisional application No. 63/139,008, filed on Jan. 19, 2021, provisional application No. 62/994,502, filed on Mar. 25, 2020.

(51) Int. Cl.
*G01H 9/00* (2006.01)
*G01D 5/353* (2006.01)
(Continued)

(52) U.S. Cl.
CPC ......... *G01H 9/004* (2013.01); *G01D 5/35316* (2013.01); *G01D 5/35361* (2013.01);
(Continued)

(58) Field of Classification Search
CPC ........ G01H 9/00; G01H 9/004; G06N 3/0464; G06N 3/048; G01D 5/35316; G01D 5/35361; H04R 23/008
See application file for complete search history.

(56) References Cited

U.S. PATENT DOCUMENTS

| 11,754,532 B2 * | 9/2023 | Ooi | A01M 1/026 |
| | | | 356/402 |
| 2009/0007670 A1 * | 1/2009 | Hawwa | G01N 29/14 |
| | | | 73/571 |

(Continued)

FOREIGN PATENT DOCUMENTS

| CN | 110751073 A | * | 2/2020 | F17D 5/00 |
| CN | 111325095 A | * | 6/2020 | G01H 17/00 |

(Continued)

OTHER PUBLICATIONS

Machine translation of CN-110751073-A (Year: 2020).*
(Continued)

*Primary Examiner* — Nguyen Q. Ha
(74) *Attorney, Agent, or Firm* — PATENT PORTFOLIO BUILDERS PLLC

(57) ABSTRACT

A fiber optic distributed acoustic sensing (DAS) system for detecting a red palm weevil (RPW) includes an optical fiber configured to be wrapped around a tree and a DAS box connected to the optical fiber. The DAS box includes a processing unit that is configured to receive a filtered Rayleigh signal reflected by the optical fiber, and run the filtered Rayleigh signal through a neural network system to determine a presence of the RPW in the tree.

20 Claims, 19 Drawing Sheets

(51) Int. Cl.
  *G06N 3/0464* (2023.01)
  *G06N 3/048* (2023.01)
  *H04R 23/00* (2006.01)

(52) U.S. Cl.
  CPC .......... *G06N 3/0464* (2023.01); *G06N 3/048* (2023.01); *H04R 23/008* (2013.01)

(56) References Cited

U.S. PATENT DOCUMENTS

| | | |
|---|---|---|
| 2018/0195883 A1 | 7/2018 | Geiger |
| 2018/0357542 A1 | 12/2018 | Wu et al. |
| 2019/0063960 A1 | 2/2019 | Ramos |
| 2019/0104715 A1 | 4/2019 | Hamozeg |

FOREIGN PATENT DOCUMENTS

| | | | | |
|---|---|---|---|---|
| JP | 2004058523 A | * | 2/2004 | ............ B29C 65/08 |
| KR | 20210074923 A | * | 6/2021 | .......... G01M 5/0066 |
| WO | 2019234516 A1 | | 12/2019 | |
| WO | 2021038407 A1 | | 3/2021 | |

OTHER PUBLICATIONS

Machine translation of CN-111325095-A (Year: 2020).*
Machine translation KR-20210074923-A (Year: 2021).*
Machine translation of JP-2004058523-A (Year: 2004).*
Bao, X., et al., "Recent Development in the Distributed Fiber Optic Acoustic and Ultrasonic Detection," Journal of Lightwave Technology, Aug. 15, 2017, vol. 35, No. 16, pp. 3256-3267, IEEE.
Bublin, M., et al., "Machine Learning for Distributed Acoustic Sensors Classic Versus Image and Deep Neural Networks Approach," ariv.org, Cornell University Library, 201 Olin Library Cornell University Ithaca, NY 14863, Apr. 25, 2019, pp. 1011.
Che, Q., et al., "Partial Discharge Recognition Based on Optical Fiber Distributed Acoustic Sensing and a Convolutional Neural Network," IEEE Access, Aug. 9, 2019, vol. 7, pp. 101758-101764, IEEE.
Farquad, M.A.H., "Machine Learning Based Early Detection of Red Palm Weevil using Remote Sensing Technology in Saudi Arabia," International Journal of Scientific Research in Computer Science, Engineering and Information Technology, May-Jun. 2018, vol. 3, Issue 5, pp. 587-595.
Hetzroni, A., et al., "Toward Practical Acoustic Red Palm Weevil Detection," Computers and Electronics in Agriculture, Mar. 19, 2016, vol. 124, pp. 100-106, Elsevier B.V.
International Search Report in corresponding/related International Application No. PCT/IB2021/051951, date of mailing Jun. 7, 2021.
Peng, Z., et al., "Big Data Analytics on Fiber-Optical Distributed Acoustic Sensing with Rayleigh Enhancements," 2019 IEEE Photonics Conference (IPC), Sep. 29, 2019, pp. 1-3, IEEE.
Shiloh, L., et al., "Efficient Processing of Distributed Acoustic Sensing Data Using a Deep Learning Approach," Journal of Lightwave Technology, Sep. 15, 2019, vol. 37, No. 18, pp. 4755-4762, IEEE.
Written Opinion of the International Searching Authority in corresponding/related International Application No. PCT/IB2021/051951, date of mailing Jun. 7, 2021.
Substantive Examination Report in corresponding/related Saudi Arabian Application No. 522440618, dated Dec. 24, 2023.

* cited by examiner

| Data | Accuracy | Precision | Recall | False Alarm |
|---|---|---|---|---|
| Temporal data, without wind | 83.6% | 94.4% | 68.6% | 5.6% |
| Spectral data, without wind | 99.3% | 99.5% | 99.0% | 0.5% |
| Spectral data, with wind | 99.6% | 99.7% | 99.5% | 0.3% |
| Spectral data, combined | 99.9% | 99.9% | 99.9% | 0.1% |

FIG. 14

| Data | Accuracy | Precision | Recall | False Alarm |
|---|---|---|---|---|
| Temporal data, without wind | 100.0% | 100.0% | 100.0% | 0.0% |
| Temporal data, with wind | 99.9% | 99.7% | 100.0% | 0.3% |
| Temporal data, combined | 99.7% | 99.5% | 99.9% | 0.5% |
| Spectral data, without wind | 99.3% | 100.0% | 98.5% | 0.0% |
| Spectral data, with wind | 98.3% | 99.5% | 97.0% | 0.5% |
| Spectral data, combined | 99.1% | 99.7% | 98.3% | 0.3% |

FIG. 18

RED PALM WEEVIL DETECTION BY APPLYING MACHINE LEARNING TO SIGNALS DETECTED WITH FIBER OPTIC DISTRIBUTED ACOUSTIC SENSING

CROSS-REFERENCE TO RELATED APPLICATIONS

This application is a U.S. National Stage of International Application No. PCT/IB2021/051951, filed on Mar. 9, 2021, which claims priority to U.S. Provisional Patent Application No. 62/994,502, filed on Mar. 25, 2020, entitled "COMBINING ARTIFICIAL INTELLIGENCE AND DISTRIBUTED FIBER OPTIC SENSING TO DETECT RED PALM WEEVIL," and U.S. Provisional Patent Application No. 63/139,008, filed on Jan. 19, 2021, entitled "COMBINING ARTIFICIAL INTELLIGENCE AND DISTRIBUTED FIBER OPTIC SENSING TO DETECT RED PALM WEEVIL," the disclosures of which are incorporated herein by reference in their entirety.

BACKGROUND

Technical Field

Embodiments of the subject matter disclosed herein generally relate to a system and method that use a fiber optic distributed acoustic sensing for detecting a red palm weevil, and more particularly, to an enhanced system that processes data recorded with the fiber optic distributed acoustic sensing with a machine learning algorithm to separate true RPW signals from ambient noise.

Discussion of the Background

Red palm weevil (RPVV) (*Rhynchophorus ferrugineus*) is a snout pest originating from tropical Asia. In the past few decades, it has spread out to many regions worldwide including North Africa, Middle East, and Mediterranean regions. This pest has wiped out many palm farms in different countries, so it is considered a very severe problem. In the Gulf countries and the Middle East, millions of dollars are spent yearly only to remove the infested palm trees. The cost to treat the infested palm trees could be even higher. Additionally, by 2023, it is estimated that the RPW control cost and loss of benefits to be in the millions of dollars in Italy, Spain, and France.

The problem with this pest is that although there are available techniques to heal RPW infested palm trees, detecting the presence of the RPW threat at an early stage (first two/three weeks of the weevil larvae stage) is challenging. This is so because by the time a palm tree shows visible signs of distress, such as a sagging canopy, this generally means that the RPW infection is well-advanced and it is too late to rescue the tree. As a result, governments of many countries are committing to develop a reliable and efficient early detection approach to tackle this problem.

There are several methods that have been reported to tackle this sever danger. For instance, trained dogs are used to smell the gases released from infested palms during the fermentation processes. Unfortunately, sensing such kind of gases is not an accurate selective process because its efficiency is impacted by the presence of other volatile products. Alternatively, infested trees are screened with a computer-based tomography system. However, this technique lacks feasibility since it is slow and expensive.

The first detectable signals of an infested tree originate from the noise produced by the weevil larvae while eating within the trunk of the tree. Therefore, the most promising early detection methods rely on using acoustic sensors. More specifically, the existing methods that use acoustic sensors, primarily insert an acoustic probe, such as microphone, into a hole drilled into a palm trunk and then the probe records the sound produced by the beetles in real-time. The sound is recorded on a computer that is connected to the acoustic probe. The differences among the methods that are using the acoustic sensor are mainly in the signal processing techniques implemented for processing the recorded sound. However, all these methods require in-situ monitoring.

A disadvantage of the aforementioned acoustic methods is the damage done to the tree because of the hole made in the trunk for inserting the sound probe, the labor necessary to drill each tree, the impact of the hole on the growth of the palms, and the possibility of other insects to establish a nest into the holes made into the trunk. Additionally, offering an acoustic sensor along with a wireless communication interface for each tree to provide continuous monitoring significantly increases the cost of the entire RPW surveillance system given that a red palm tree orchard can have thousands of such trees.

A more advanced solution was proposed in [2], International Patent Application PCT/IB2020/057865, filed on Aug. 21, 2020, and assigned to the assignee of the present application (the entire content of which is incorporated herein by reference). According to this application, an optical fiber 100 can be distributed along one or more trees 110 as shown in FIG. 1. More specifically, if plural trees are to be monitored, a distributed acoustic sensor (DAS) box 120 is connected to the single optical fiber 110, and the fiber extends to the plural trees 110-I-I, where I is any integer equal to or larger than one. The same optical fiber 110 can be rolled around each tree 110-I, for example, from the ground up to about 1 m height on the trunk of the tree, where the probability of finding the RPW larva is the highest. However, other heights may be used. Between the trees, the optical fiber cable can be either laid down on the ground or buried into the soil, based on the environmental conditions.

This RPW detection technique could still face challenges during a feasibility-phase for the actual farms. This is because there could be many noise sources within and around an RPW infested tree that could trigger false alarms. For instance, other insects including armored scales and borer generate sounds, which might interfere with that of the RPW. Additionally, sound and mechanical vibrations produced by birds, digging, watering, etc. would also be captured by the DAS system. These noise sources would generate false alarms, which is a major drawback for any sensing system.

Thus, there is a need for a new DAS system that is capable of detecting not only the presence of the RPW larvae, but also to discern between the RPW sound and the ambient sound, with minimal infrastructure investment and support, to reduce the number of false alarms.

BRIEF SUMMARY OF THE INVENTION

According to an embodiment, there is a fiber optic distributed acoustic sensing (DAS) system for detecting a red palm weevil (RPW), and the DAS system includes an optical fiber configured to be wrapped around a tree and a DAS box connected to the optical fiber. The DAS box includes a processing unit that is configured to receive a filtered Rayleigh signal reflected by the optical fiber and run the filtered Rayleigh signal through a neural network system to determine a presence of the RPW in the tree.

According to another embodiment, there is a method for detecting a red palm weevil with a fiber optic DAS system and the method includes sending a modulated signal through an optical fiber that is wrapped around a tree, receiving at a DAS box, which is connected to the optical fiber, a reflected Rayleigh signal, which is a reflection of the modulated signal by the optical fiber, filtering the reflected Rayleigh signal with a fiber Bragg grating configured to receive and filter the reflected Rayleigh signal to generate a filtered Rayleigh signal, and processing the filtered Rayleigh signal with a neural network system to determine a presence of the RPW in the tree.

According to yet another embodiment, there is a DAS box for detecting a red palm weevil and the DAS box includes a light source configured to generate a continuous-wave light, a light modulator configured to modulate an amplitude of the continuous-wave light emitted by the light source to generate a modulated light, a circulator configured to receive the modulated light and inject the modulated light into an optical fiber, a processing unit that is configured to receive a filtered Rayleigh signal reflected by the optical fiber, and a fully connected artificial neural network (ANN) or a convolutional neural network (CNN) system configured to process the filtered Rayleigh signal to determine a presence of the RPW in the tree.

BRIEF DESCRIPTION OF THE DRAWINGS

For a more complete understanding of the present invention, reference is now made to the following descriptions taken in conjunction with the accompanying drawings, in which:

FIG. 14 shows the performance of the artificial neural network for various environmental conditions;

FIG. 18 illustrates the performance of the convolutional neural network for various environmental conditions.

DETAILED DESCRIPTION OF THE INVENTION

Figure 1:
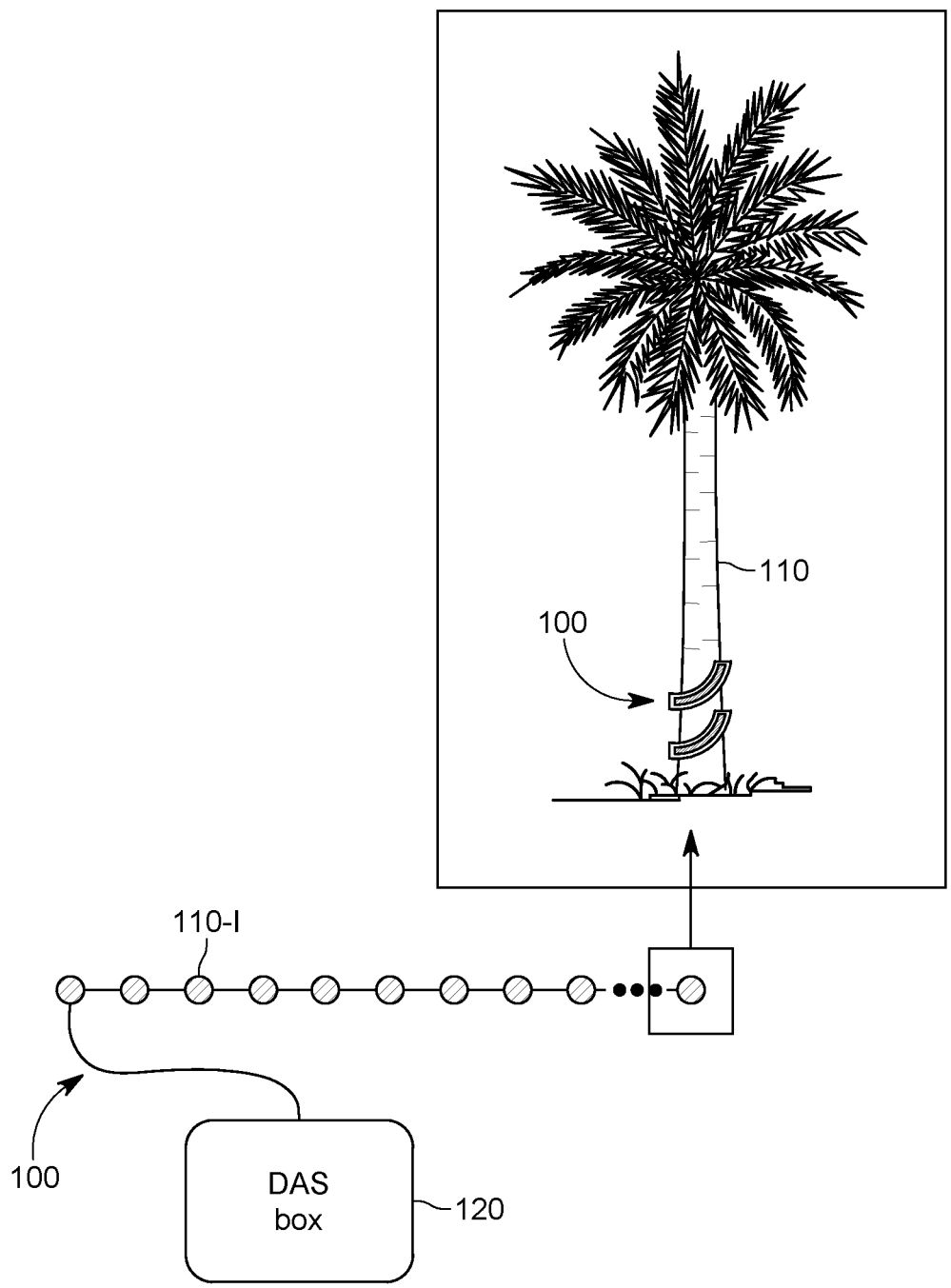
FIG. 1 is a schematic diagram of a distributed acoustic sensor system that is used to monitor a tree.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a DAS system provided with a machine learning algorithm that is used to separate the RPW larvae generated noise from the ambient noise. However, the embodiments to be discussed next are not limited to determining the presence of the RPW larvae, or to using only a machine learning algorithm, but can be used for detecting other organisms.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, an optical fiber DAS is introduced that is programmed to also run a machine algorithm to separate environmental noises from the RPW generated noise. Prior to discussing the new system, the possible components of the DAS box in one application are introduced. The underlying operation concept of an optical fiber DAS relies on using a coherent (narrow linewidth) laser source to launch optical pulses into the optical fiber. While a pulse of light is propagating along the optical fiber, this pulse of light can experience a scattering while inside the optical fiber, and then a back pulse is generated and this back pulse propagates in an opposite direction along the optical fiber relative to the original pulse of light. The back pulse can be a Rayleigh scattering when the interaction between the initial pulse of light and the optical fiber is elastic, and/or the back pulse is Stokes Raman and/or Anti-Stokes Raman when the interaction is inelastic. The backscattered pulses (Rayleigh, Stokes-Raman, or Anti-Stokes Raman) propagate backwards along the optical fiber and they are received at the fiber input port of the DAS box for storage and processing. By monitoring the intensity's temporal evolution of the recorded backscattered pulses, it is possible to (1) remove part of the signal that is associated with the ambient noise and (2) to accurately calculate a position along the optical fiber, which was subjected to an acoustic signal and to determine its frequency. Based on these responses, a processing part of the DAS system can be configured to determine whether the RPW is present in the tree. In the following, for simplicity, the backscattered pulses are considered to be Rayleigh pulses. However, the embodiment discussed herein are applicable to any backscattered pulses.

Figure 2:
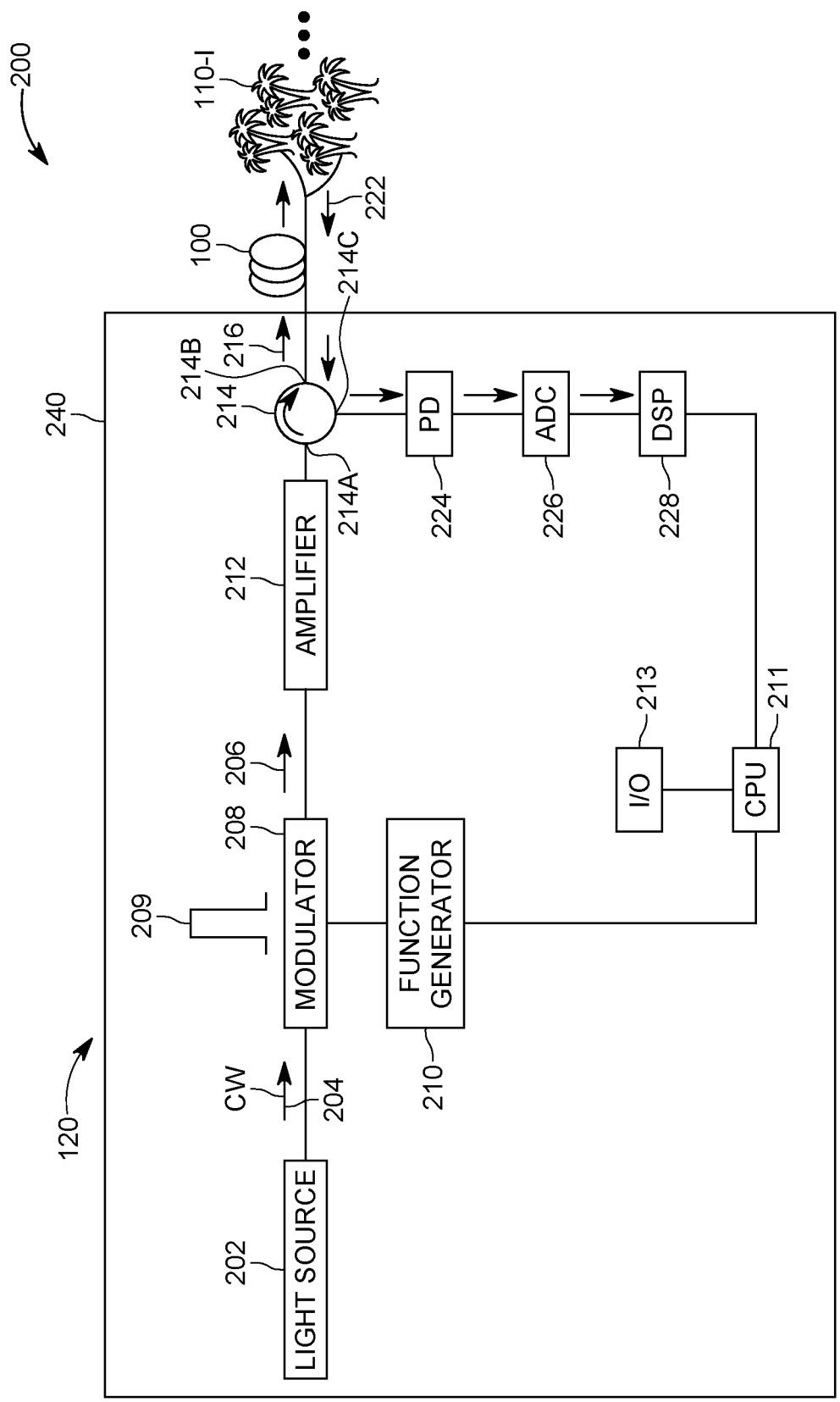
FIG. 2 is a schematic diagram of a distributed acoustic sensor box that is configured to send a modulated optical signal into an optical fiber.

In this regard, FIG. 2 shows a fiber optic DAS system 200 that is capable of measuring a strain exerted on the optical fiber by changes in pressure, temperature and/or acoustic noise. System 200 has two main components, the DAS box 120 and the optical fiber 100, which is connected to the DAS box 120. The DAS box 120 includes all the electronics for generating a light beam, sending the light beam into the optical fiber, receiving a reflected light from the optical fiber, and processing the reflected light for detecting the RPW. More specifically, the DAS box 120 includes a light source 202 that is configured to generate continuous-wave (CW) light 204 that is coherent. For example, the light source 202 may be a laser or a light-emitting diode. The CW light 204 is converted to optical pulses 206 via a light modulator 208. The light modulator 208 is connected to a function generator 210. The function generator 210, which can be controlled by a computing device 211, is configured to generate a mathematical function to be applied to the modulator to modulate the light 204. For example, FIG. 2 shows the modulator 208 applying a rectangular pulse 209 to the light 204, to obtain the optical pulses 206 (or modulated light). Other shapes may be used for the pulse 209. The computing device 211 is also connected to an input/output module 213, which is capable of communicating, for example, in a wireless or wired manner with a smartphone, personal computer, or any other electronic device for both sending messages and also for receiving instructions/commands.

Optionally, the system 200 includes an amplifier 212 for amplifying the modulated light 206, prior to launching it through a circulator 214 into the optical fiber 100. FIG. 2 schematically shows the optical fiber 100 being directed to plural trees 110-I. The circulator 214 may be, for example, a three- or four-port optical device designed such that light entering any port exits from the next port. This means that if light enters a first port 214A, it is emitted from a second port 214B. However, if some of the emitted light 216 is reflected back to the circulator 214, it does not come out of the first port 214A, but instead exits from a third port 214C. This makes possible that a reflected Rayleigh signal 222, after reaching the circulator 214, is directed toward a photodetector 224, instead of being sent toward the amplifier 212.

While the optical pulse 216 is propagating along the fiber 100, the Rayleigh signal 222 is backscattered from the trees 110-I. In the backward direction, the Rayleigh signal is recorded via the photodetector 224 and then sampled using an analog-to-digital converter (ADC) 226. A digital signal processing (DSP) 228 may be used to filter out the RPW sounds in the frequency domain and exactly identifies the locations of the infected palm trees 110-I using, for example, the time domain signal.

The optical fiber 100 may be a single-mode fiber (SMF). At the fiber input port, consecutive Rayleigh backscattered traces are recorded in the time domain. Each Rayleigh trace has a speckle-like profile because of coherent interference of the signals reflected by scattering centers within the injected pulse duration. In the absence of intrusions along the optical fiber, i.e., no refractive index perturbation, the recorded Rayleigh traces are ideally identical. In the case that an acoustic signal is applied at a position along the fiber, such as the weevil larvae sound, the effective refractive index of the fiber changes at this position and consequently, the intrusion could be sensed by observing the intensity fluctuations of its corresponding speckle in the recorded traces.

By monitoring the intensity temporal evolution of the recorded Rayleigh signals 222, one can accurately figure out a position along the optical fiber 100 which was subjected to an acoustic signal emitted by the RPW and thus, determine the location of the RPW. For the purpose of RPW early detection, the system 200 shown in FIG. 2 outweighs the existing acoustic sensors in the literature because of at least one of the following reasons: 1) it would provide non-stop monitoring for palm trees with a relatively low price, 2) the sensing length of the typical optical fiber DAS is around 10 km, which could cover spacious farm area, 3) by using an optical switch and time-division-multiplexing (TDM), several fibers can be attached to the same DAS box, in case that monitoring larger farm areas is demanded, 4) no invasive sensing is required since the optical fiber would be wounded externally around the palms, and 5) the optical fiber used for acoustic sensing can simultaneously monitor ambient temperatures, with a resolution less than 0.1° C., which is considerably important to control farm fires, which is another major problem around the world.

In one embodiment, all the elements of the system 200, except the optical fiber 100, may be placed in a single housing 240. This means that all of the optical components such as laser, photodetector, etc., are gathered within the DAS box, for example, at a control master station, whereas only the optical fiber 100 is wounded around the palm trees 110-I in a form of an optical network.

Figure 3A:
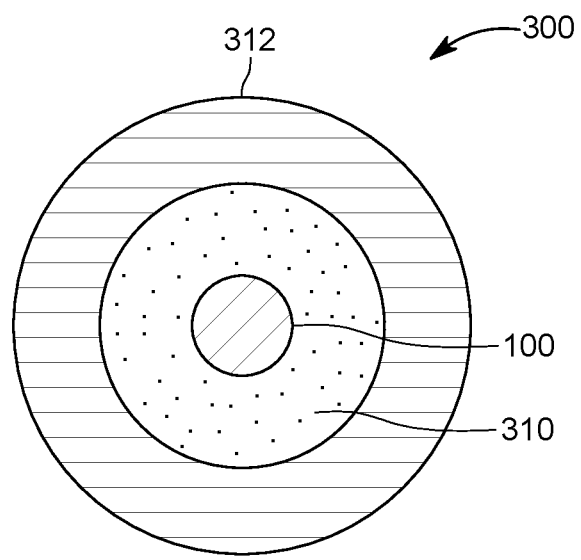
FIGS. 3A to 3B illustrate various implementations of the distributed acoustic sensor system.
Figure 3B:
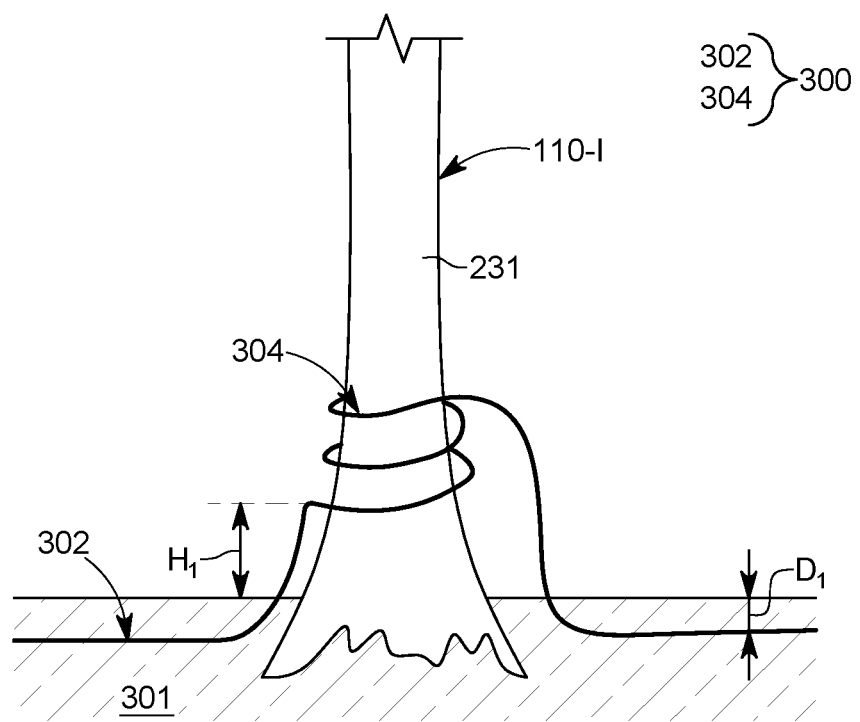

The optical fiber 100 may be wounded around the trunk of the tree 110-I by itself, as shown in FIG. 1, or protected by a cover layer as illustrated in FIGS. 3A and 3B. More specifically, FIG. 3A shows the optical fiber 100 being completely surrounded by a filler material 310, for example, cotton or similar fiber material, and an exterior shield layer 312. This optical fiber assembly 300 may have the exterior shield layer 312 made to fully enclose the filler material and the optical fiber. The exterior shield layer 312 may be made from a rigid material (e.g., steel tube or pipe, plastic pipe) or from a flexible material (e.g., flexible metallic or plastic pipe, etc.). In one embodiment, the exterior shield layer 312 is rigid for a portion of the optical fiber and flexible for another portion of the optical fiber.

For example, as illustrated in FIG. 3B, the optical fiber assembly 300 has a first portion 302 that is fully buried in the ground 301, and a second portion 304 that is wounded around the trunk 231 of the tree 110-I. The first portion 302 may be made to be rigid while the second part 304 may be made to be flexible, to allow it to wound around the trunk of the tree. The purpose of the filler material and the exterior shield layer 312 is to protect the optical fiber 100 from mechanical or thermal damage while being deployed in the field. In this regard, note that in a farm there is heavy equipment that move around the trees for various agricultural procedures. In one application, the depth D1 at which the first portion 302 is buried into the ground is between 0.5 to 2 m. A height H1 at which the optical fiber assembly starts to wound around the trunk 231 is about 0.5 to 3 m for best efficiency, as the weevil larva tends to attack the trunk at these heights. A length of the optical fiber 100 that is present in the second portion 304 is between 1 and 10 m. Other numbers for the parameters discussed herein may be used. However, one or more portions of the optical fiber may be directly exposed to the ambient, at desired locations between the trees, to be able to detect the temperature and moisture of the ambient.

Figure 4:
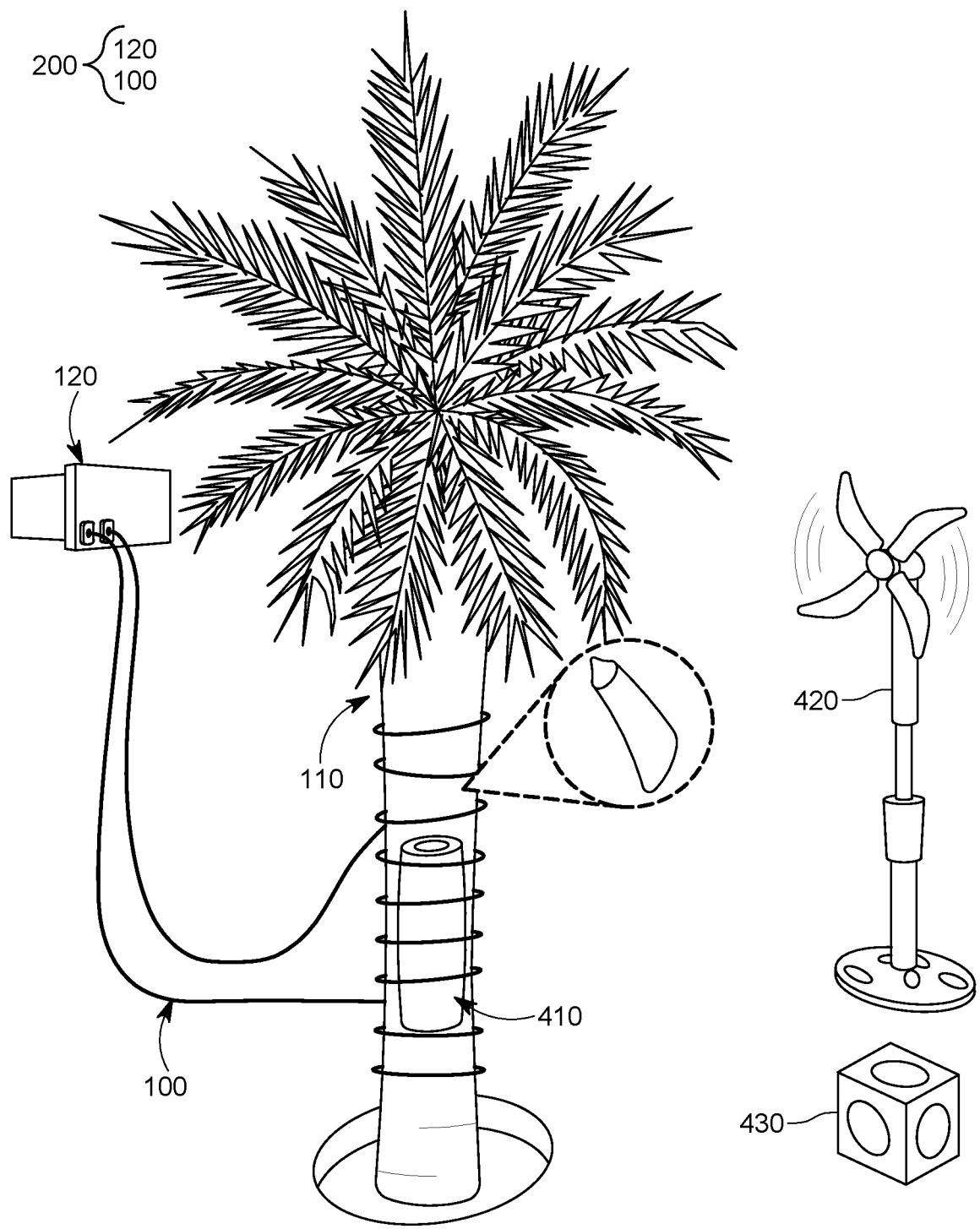
FIG. 4 illustrates a configuration of the distributed acoustic sensor system that is used for evaluating the influence of ambient noise on the recorded Rayleigh signal.

The DAS system 200 might not be well equipped to separate the RPW larvae noise from the environmental noise. Thus, the DAS system 200 was modified and used in a lab to detect an actual RPW larvae in a palm tree while ambient noise is artificially generated. FIG. 4 shows the overall configuration of this embodiment. The optical and electronic components of the DAS system 200 are assembled within the DAS box 120. The output light from the DAS box 120 is launched into the single-mode fiber (SMF) 100, and the fiber is wound around the tree trunk 110. Within the trunk of the tree 110, a loudspeaker 410 was placed that continuously plays an eating sound that is similar to the sound generated by a 12-day old weevil larvae. At about 1 m distance from the tree 110, a fan 420 was provided to blow air towards the optical fiber 100 and the tree 110, to simulate the wind in an actual palm tree farm. Another loudspeaker 430 was installed away from the tree 110, to simulate bird sounds. The wind and the bird sounds constitute the ambient noise that is recorded by the optical fiber 100 together with the sound generated by the RPW.

Figure 5:
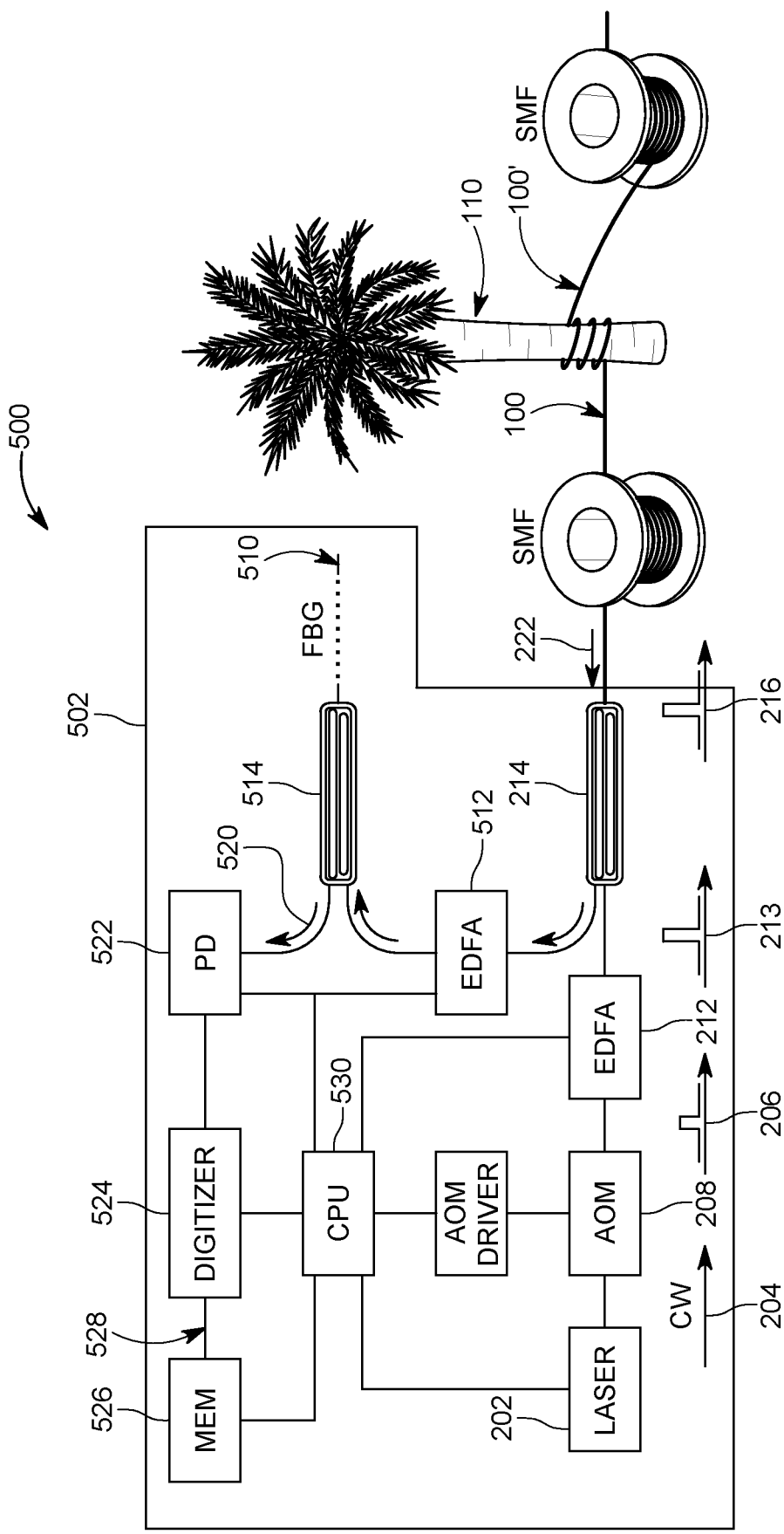
FIG. 5 is a schematic diagram of a distributed acoustic sensor box that is configured to apply convolutional neural network processing for distinguishing between signals associated with the RPW larvae and signals associated with an ambient noise.

The DAS box includes an interrogation system of the fiber optic 100, which is designed using the phase-sensitive optical time-domain reflectometry ((p-OTDR) [1]. In this embodiment, the system 500 shown in FIG. 5 was used and it includes the DAS box 502 and the fiber optic 100. The DAS box 502 is configured so that a narrow linewidth laser generates a continuous wave (CW) light 204 of 100-Hz linewidth having a 40-mW optical power. The laser light 204 is then converted into optical pulses 206 using an acousto-optic modulator (AOM) 208 that produces the pulses 206 having a 50-ns width and a 5-kHz repetition rate. The selected pulse width makes the DAS system 500 to have a 5-m spatial resolution. The power of the optical pulses 206 is amplified using an erbium-doped fiber amplifier (EDFA) 212, while its output light 213 is launched through a circulator 214 into the SMF 100 of about 2-km length. At about 1-km distance from the input port of the SMF, a 5-m section of the fiber is wrapped around the tree 110's trunk. The backscattered signal 222 from the SMF is amplified with another EDFA 512 and then sent to a second circulator 514. The signal is then sent to a fiber Bragg grating (FBG) 510, which discards the amplified spontaneous emission (ASE) noise. The filtered Rayleigh signal 520 is detected by a photodetector (PD) 522 and sampled by a digitizer 524 having a 200-MHz sampling rate. The sampled Rayleigh signals 528 are then recorded as 1-s periods (5000 traces per period) and stored in a memory device 526. A processing unit 530, for example, a microprocessor, may be connected to the elements discussed herein for coordinating their actions. While FIG. 5 shows the processing unit 530 being part of the DAS box 502, in one embodiment it is possible that the processing unit is external to the DAS box, e.g., being a remote server that does the calculations required by the DAS box. This embodiment uses two separate standard SMFs 100 and 100', protected with different jackets of a 900-μm diameter (denoted as "JKT1") and a 5-mm diameter (denoted as "JKT2"), respectively. In one embodiment, the thickness of the JKT1 and JKT2 can vary by +1-20% and still achieve the same effect. Note that only one SMF is necessary for determining the RPW presence. The optical fibers having the JKT1 configuration or the one having the JKT2 configuration are used as alternatives for identifying the most appropriate one for detecting the RPW larvae.

Figure 6:
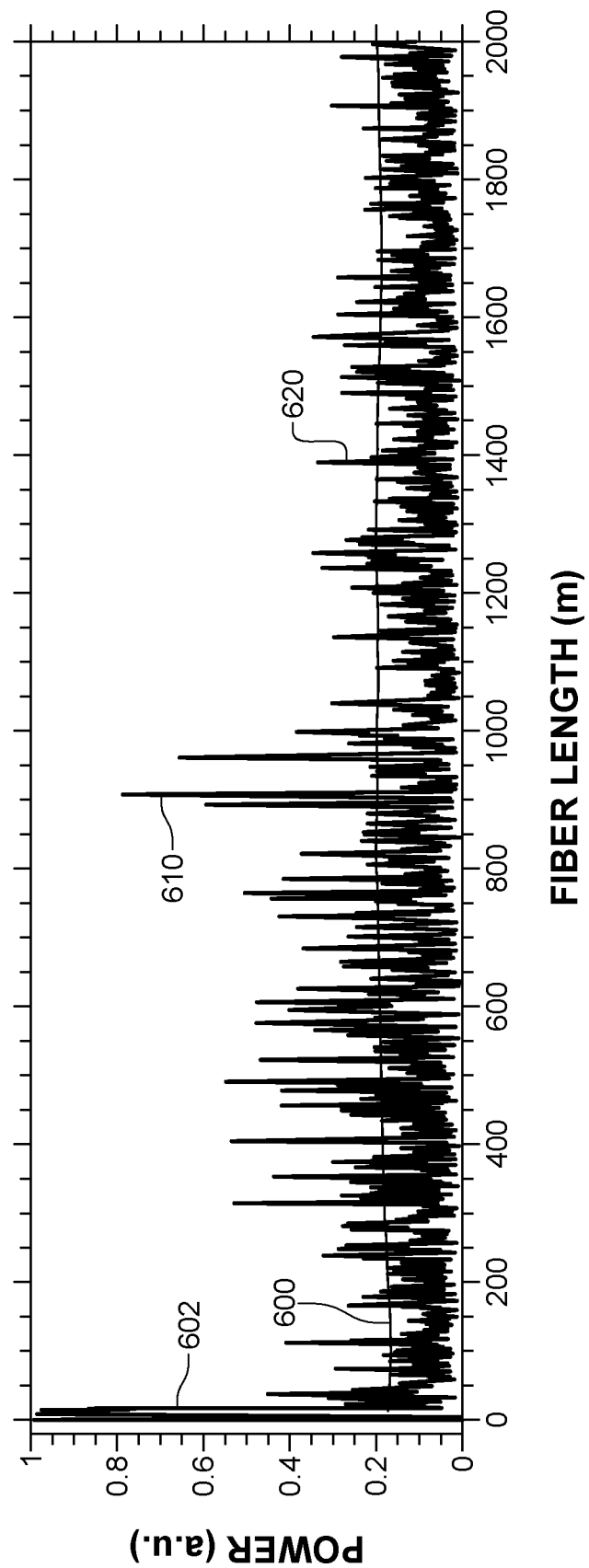
FIG. 6 illustrates a Rayleigh trace recorded with the distributed acoustic sensor box.

FIG. 6 shows an example of a Rayleigh trace 600 recorded by the fiber optic DAS system 500 under ideal conditions, i.e., no ambient noise. The high-power signal 602 located at the start of the SMF corresponds to the Fresnel reflection from the front facet of the SMF. Under this ideal scenario, when there is no refractive index perturbation along the SMF, the shape of the Rayleigh trace 600 remains stationary in the time-domain, for all the spatial points along the entire fiber. Consequently, the differences between the temporal subsequent Rayleigh traces and an initial reference signal are ideally zeros. In contrast, the presence of a larvae sound within the tree trunk can modulate the fiber's refractive index at the tree position, which results in changing the corresponding temporal Rayleigh signal 610 only at the tree location. By applying the normalized differential method and fast Fourier transform (FFT) to the temporal Rayleigh traces, the location of an infested tree and the larvae sound's frequencies can be identified, respectively. However, when the ambient noise is present, in addition to the Rayleigh signal corresponding to the tree location, many other signals appear 620, as shown in FIG. 6, which can mask the larvae's generated signal or produce false alarms.

Possible ways of mitigating the environmental noises, such as wind and bird sounds, which may degrade the performance of the fiber optic DAS system when detecting the RPW, are now discussed. One suggested technique of reducing the noise includes applying a spectral band-pass filter to alleviate the noise level within the recorded signals, and further trying various optical fiber's jackets which might be shaken because of the wind.

Figure 7A:
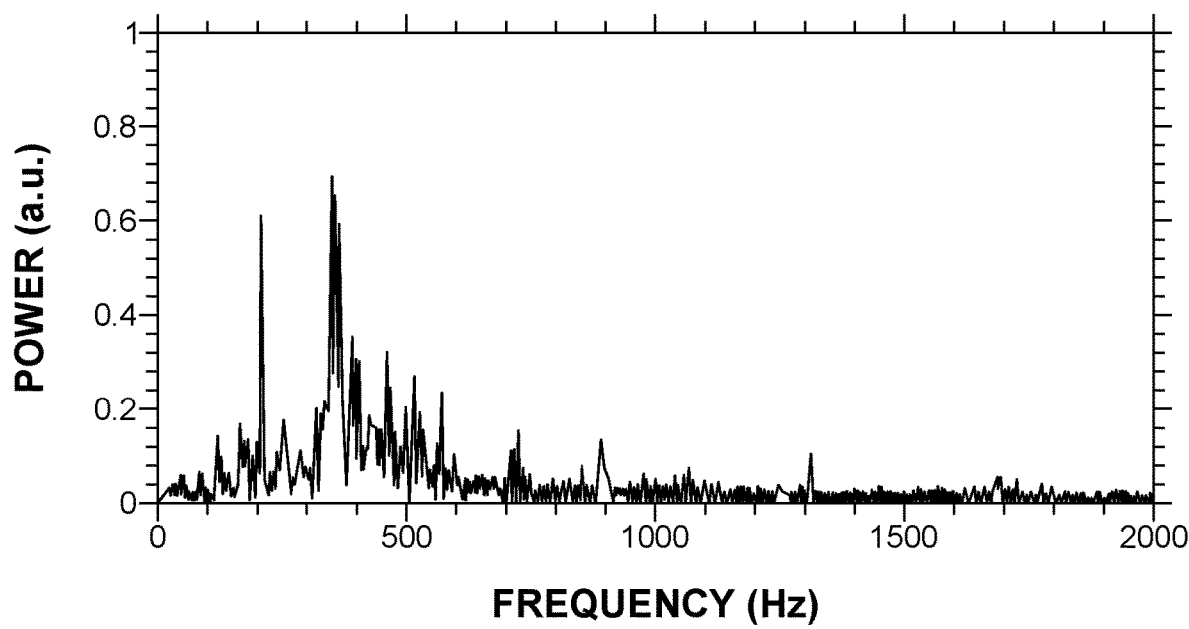
FIGS. 7A and 7B illustrate the sound spectra generated by the RPW larvae.
Figure 7B:
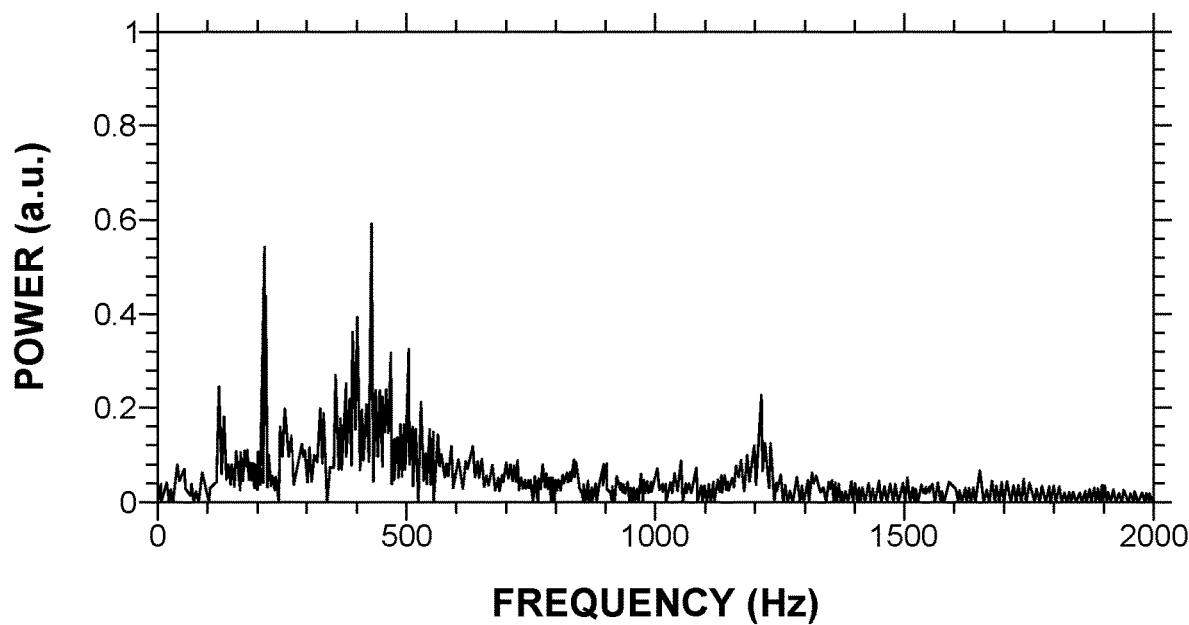

Firstly, the spectral components of the actual larvae sound are explored. In particular, a commercial voice recorder is implanted inside a truly infested tree trunk, next to about 12-day old larvae, and the noise produced by them is recorded, as shown in FIGS. 7A and 7B. The age of the larvae can be well controlled via an artificial infestation process, where it is carried out in a secured research facility to avoid spreading the RPW to other healthy trees. It is observed that the larvae almost continuously produce the sound while they are chewing the tree trunk. FIGS. 7A and 7B show two representative examples of the larvae sound's power spectra, where each corresponds to a 0.5-s recording interval. From the recordings in the figures, it is reasonable to assume that the majority of the larvae sound's optical power has frequencies below 800 Hz. In addition, it is also important to discard the low vibration frequency components below the 200 Hz to cancel the inevitable mechanical vibrations in the laboratory and the tree swinging caused by the wind. Thus, for the measurements performed with the configuration shown in FIGS. 4 and 5, a [200 Hz-800 Hz] band-pass filter is applied to the temporal vibration data that is collected using the fiber optic DAS, to enhance the signal-to-noise ratio (SNR) of the system.

Figure 8A:
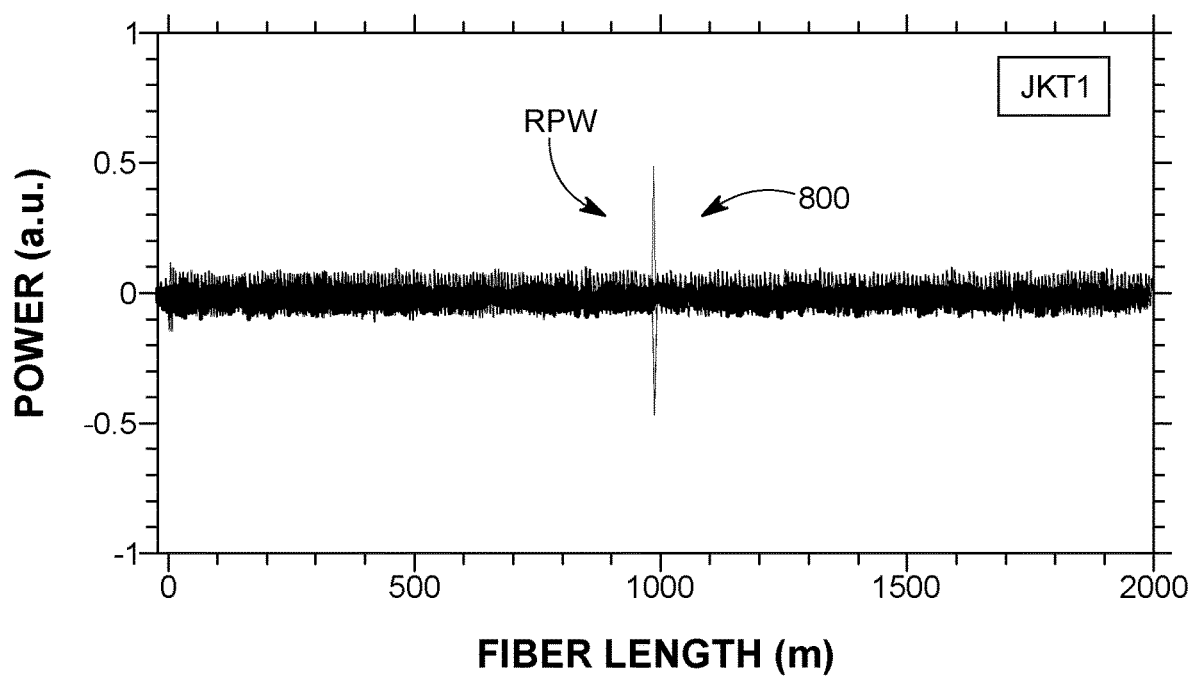
FIGS. 8A and 8B illustrate signals recorded with the distributed acoustic sensor box for infested trees when using different diameter jackets for the optical fiber and no ambient noise.
Figure 8B:
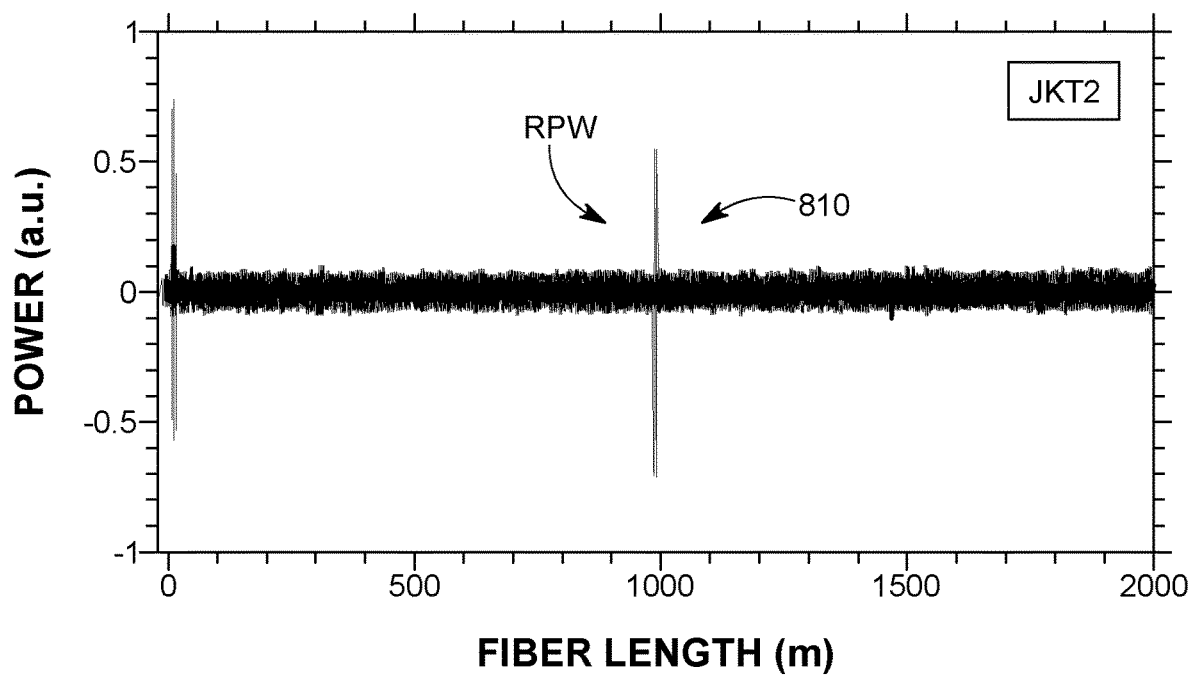

Next, the configuration shown in FIG. 4 has been used with the fan 420 and the noise loudspeaker 430 switched off, while only the larvae sound generated by the loudspeaker 410 implanted inside the tree trunk 110 was kept on. FIGS. 8A and 8B show two representative examples of the normalized differential time-domain signals 800 and 810 recorded using the DAS system 500, followed by applying the [200 Hz-800 Hz] band-pass filter, when using the SMF 100 with the JKT1 and JKT2 configurations, respectively. The two fibers accurately locate the position of the infested tree at about 1 km distance from the input ports of the fiber. The other noisy signals, which sometimes appear at the start of the SMFs, are a result of the fiber front facet's reflection.

Figure 9A:
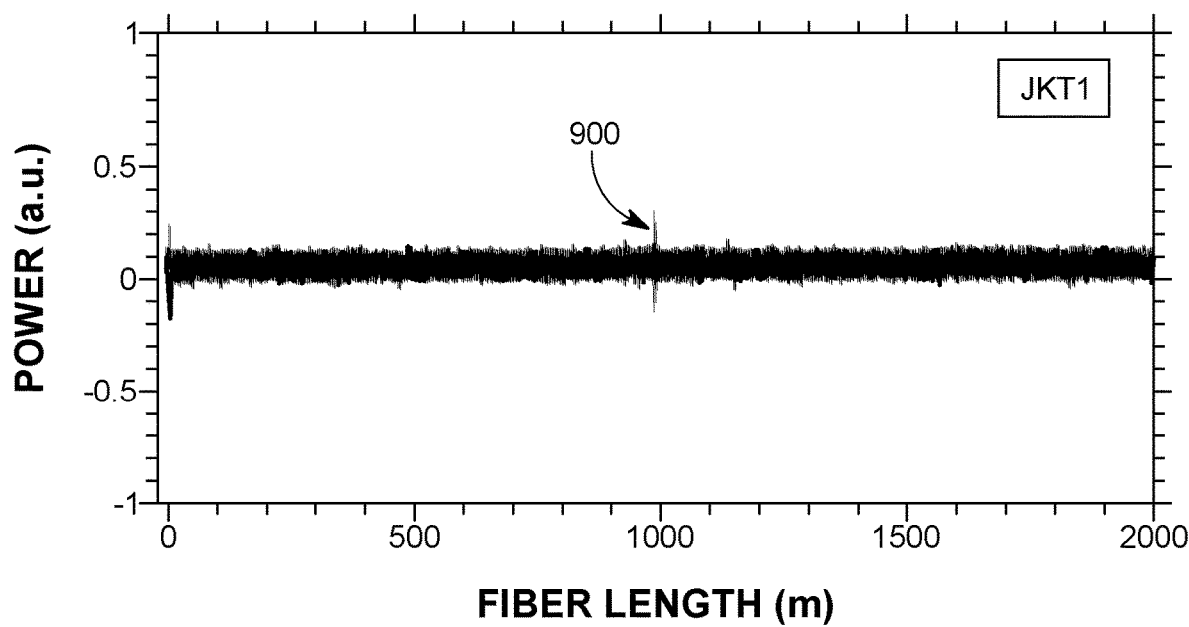
FIGS. 9A and 9B illustrate signals recorded with the distributed acoustic sensor box for infested trees when using different diameter jackets for the optical fiber with simulated wind generated noise.

Next, the two loudspeakers 410 and 430 are switched off and only the fan 420 is turned on to determine the impact of the wind on the SMF 100. The wind is considered to be the primary noise source in open-air farms, especially because the fiber 100 is wrapped around the trunk of the three, which means that the fiber is directly subjected to the wind. Even with applying the [200 Hz-800 Hz] band-pass filter, the SMF 100 with the JKT1 is impacted by the wind to produce temporal vibrations as those shown in FIG. 9A. The low frequency vibrations, produced by tree swinging as a result of the wind, can be discarded with filtering out the frequencies below 200 Hz. However, when the wind is blowing to directly hit the optical fiber 100, it results in shacking the fiber with frequencies that depend on the thickness and material of the fiber's jacket. As shown in FIG. 9A, the SMF with JKT1, which has a relatively small diameter (900-μm), produces vibration signals 900, which are caused by the wind, and these signals may resemble those generated by the larvae. This behavior may confuse the machine learning algorithms during distinguishing the healthy trees from the infested trees.

Figure 9B:
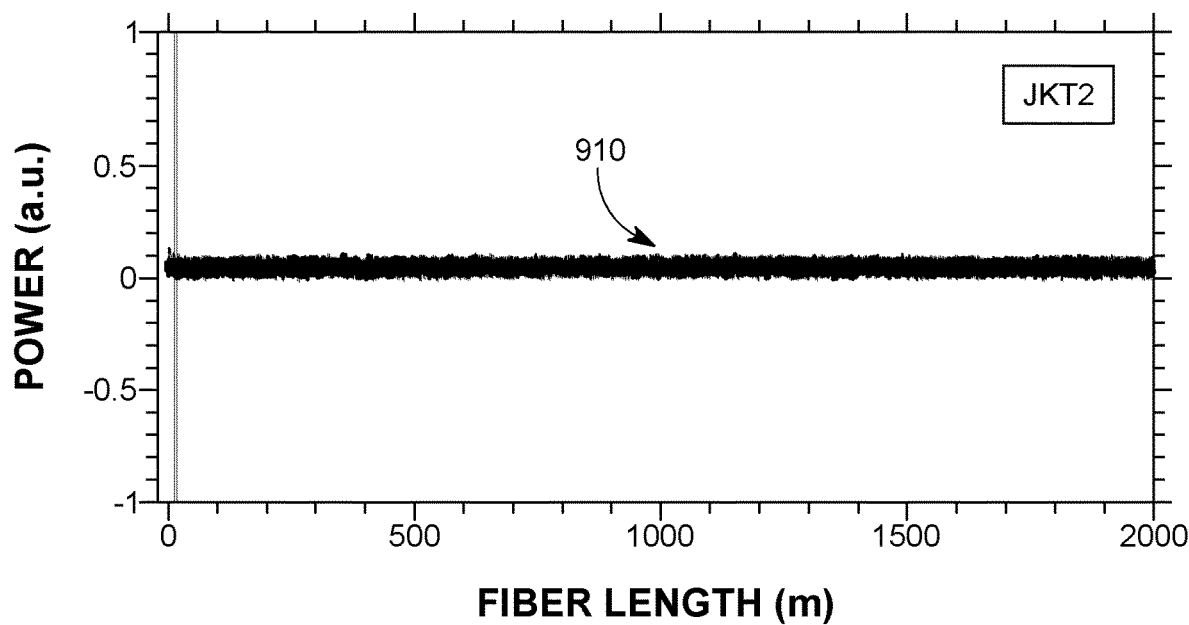

However, when the DAS box 502 is used with the SMF having the JKT2 configuration, because the JKT2 is relatively thick (5-mm diameter), the fiber rarely generates shacking frequencies within the [200 Hz-800 Hz] range because of the wind, as shown by the recorded signal 910 in FIG. 9B. Comparing the fibers with the two different jackets in terms of mitigating the noise produced by the wind helps in determining the proper optical fiber cable that can be used for real farms. Besides, when compared with the JKT1 configuration, the JKT2 has an additional advantage that it is durable enough to sustain the harsh environmental conditions of farming and the SMF inside the JKT2 cannot be easily broken by, for example, stepping on the fiber by farmers.

Figure 10A:
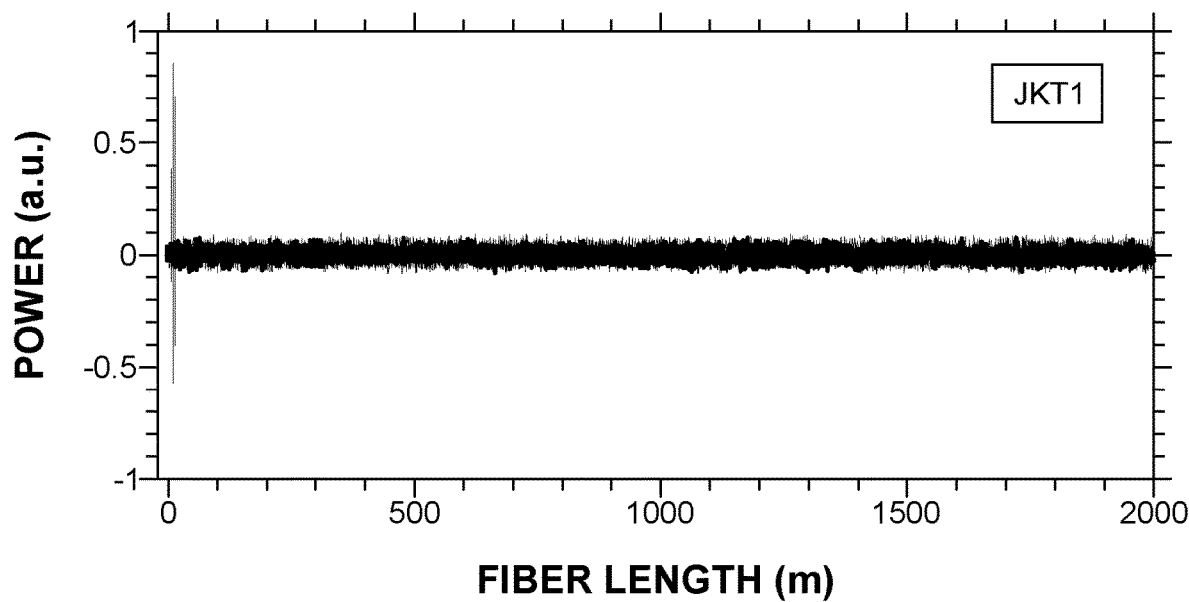
FIGS. 10A and 10B illustrate signals recorded with the distributed acoustic sensor box for infested trees when using different diameter jackets for the optical fiber with simulated bird noise.
Figure 10B:
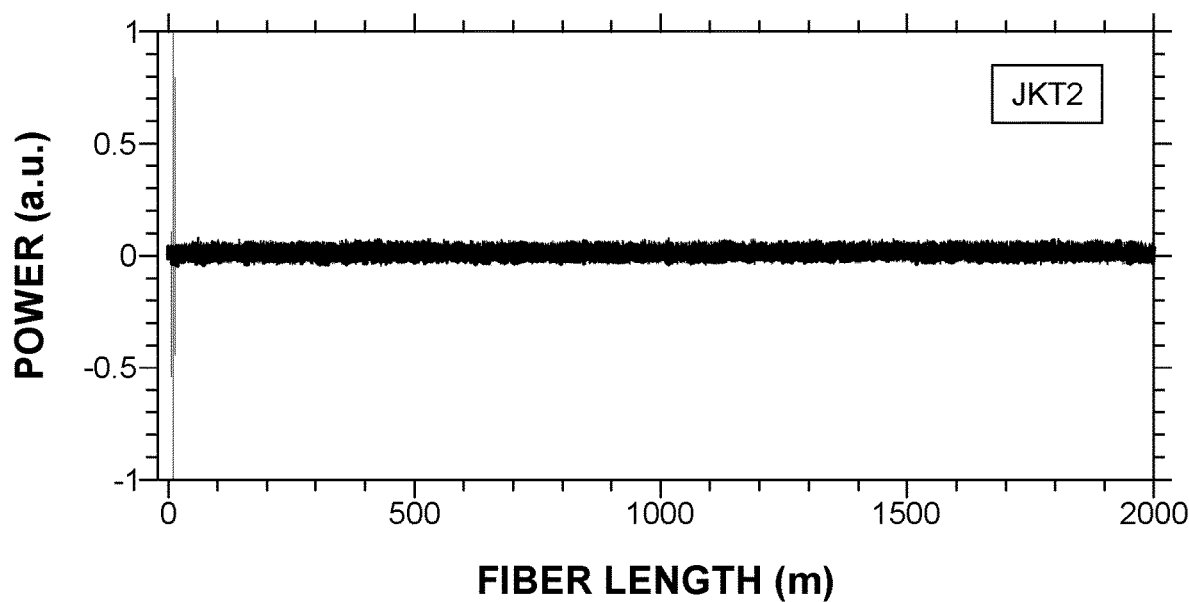

Next, the impact of the noise produced by the bird on the optical fiber was investigated. In particular, the larvae sound's loudspeaker 410 and the fan 420 were switched off, while the outside loudspeaker 430 was played continuously to generate bird sounds with a volume roughly equal to what is present in the farms. It is noted that the two SMFs with JKT1 and JKT2 cannot "hear" the bird sounds, as shown respectively in FIGS. 10A and 10B. This is because the air between the loudspeaker 430 and the optical fiber jackets significantly attenuates the vibration energy of the bird sounds.

With these observations, machine learning methods trained through supervised learning are now implemented in the DAS box 502 for distinguishing between the infested and healthy trees. Machine learning can reveal patterns associated with the larvae sound and simultaneously deal with the large amount of data produced by the DAS box 502. In this embodiment, the efficiencies of classifying the healthy and infested trees are compared when using the time- and frequency-domain data as separate inputs to neural networks, which are designed using fully-connected artificial neural network (ANN) and convolutional neural network (CNN) architectures. Given the aforementioned advantages of the SMF with the JKT2, this configuration has been used for classifying the healthy and infested trees using machine learning methods.

How to organize and label the time- and frequency-domain data for the ANN is discussed first. As previously discussed, a 5-m section of the fiber 100 is wrapped around the tree, while the DAS box is sampling the data at a 200-MHz frequency. Consequently, given the time-of-flight within the sensing system 502, the optical fiber section around the tree is represented by 10 spatial points. For each point, the digitizer reading takes a 1-s period, i.e., 5,000 readings in the time-domain per one reading period because the pulse repetition rate is 5 kHz. Since the digital band-pass filter typically distorts a short-interval at the beginning of the time-domain signal, the first 250 time-domain readings are discarded for each spatial point. Thus, the collected temporal data in each trial are organized as a vector of 47,500 length (concatenating 4,750 time-domain readings×10 spatial points). In contrast, by applying the FFT to the time-domain data of each spatial point, 2,375 frequency components are obtained. Subsequently, the spectral data of each trial is organized as a vector of 23,750 length (concatenating 2,375 frequency components×10 spatial points).

The data is labeled as "infested" or "healthy" tree, based on the SNR value of the acoustic signal at the tree position. The SNR in this embodiment is defined as the ratio between the root-mean-square (RMS) value of the time-domain signal, at the tree position, and the value of the time-domain at a reference fiber section having a 5-m length. The ability of the machine learning algorithms to classify the infested and healthy trees is evaluated in two cases, without and with the presence of the wind. Considering the first case, i.e., no wind, only the loudspeaker 410 within the tree trunk is played, while the outside loudspeaker 430 and the fan 420 are stopped, to generate signals corresponding to an infested tree. If the SNR>2 dB, the minimum acceptable SNR of a DAS system, the system records and labels the signal as "infested." 2,000 examples of the infested signals are collected in this embodiment with the volume of the larvae loudspeaker 410 set at various values below and above the level at which humans can hear the larvae sound under acceptable environmental noise. In contrast, another 2,000 samples are recorded for the "healthy" signals, when the larvae loudspeaker 410 and fan are off. The "healthy" signal examples are recorded regardless of whether the SNR value is higher or lower than the 2-dB threshold.

Next, it is desired to label the data when considering the presence of the wind. Thus, for this phase, the larvae loudspeaker 410 and the fan 420 are turned on simultaneously to record the examples of the "infested" signals. Another 2,000 various samples are recorded when the SNR values exceed the 2-dB threshold. Next, the larvae speaker 410 is switched off while keeping on the fan 420 to record another 2,000 samples, regardless of the SNR values, which correspond to the healthy tree.

Figure 11:
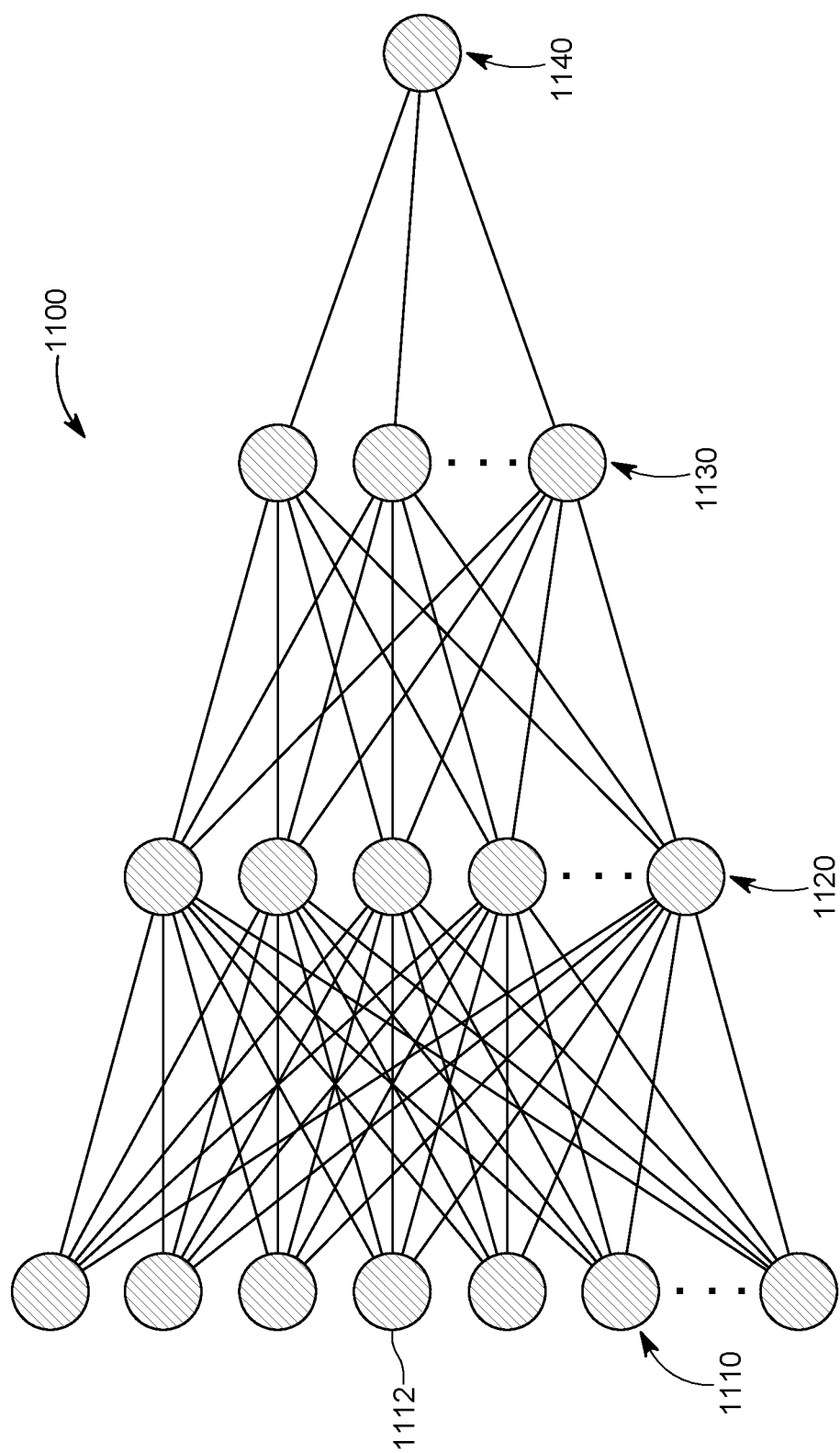
FIG. 11 schematically illustrates the configuration of an artificial neural network that is used with the distributed acoustic sensor box.

The ANN models used to handle the time- and frequency-domain data have a similar architecture 1100, which is shown in FIG. 11. This structure includes one input layer 1110, two hidden layers 1120 and 1130, and one output layer 1140. The number of nodes 1112 in the input layer 1110 matches the number of elements in the data vectors, i.e., 47,500 and 23,750 for the time- and frequency-domain data, respectively. Besides, the first hidden layer 1120 includes 500 nodes and the second hidden layer 1130 includes 50 nodes. The number of nodes has been determined by repeated trials to maximize the classification accuracy. At the end of the fully-connected ANN system, there is an output layer 1140 of one node for the binary classification (infested or healthy). Regarding the activation functions in each layer, this embodiment used the rectified linear unit (ReLU) for the hidden layers and the sigmoid function for the output layer.

Figure 12A:
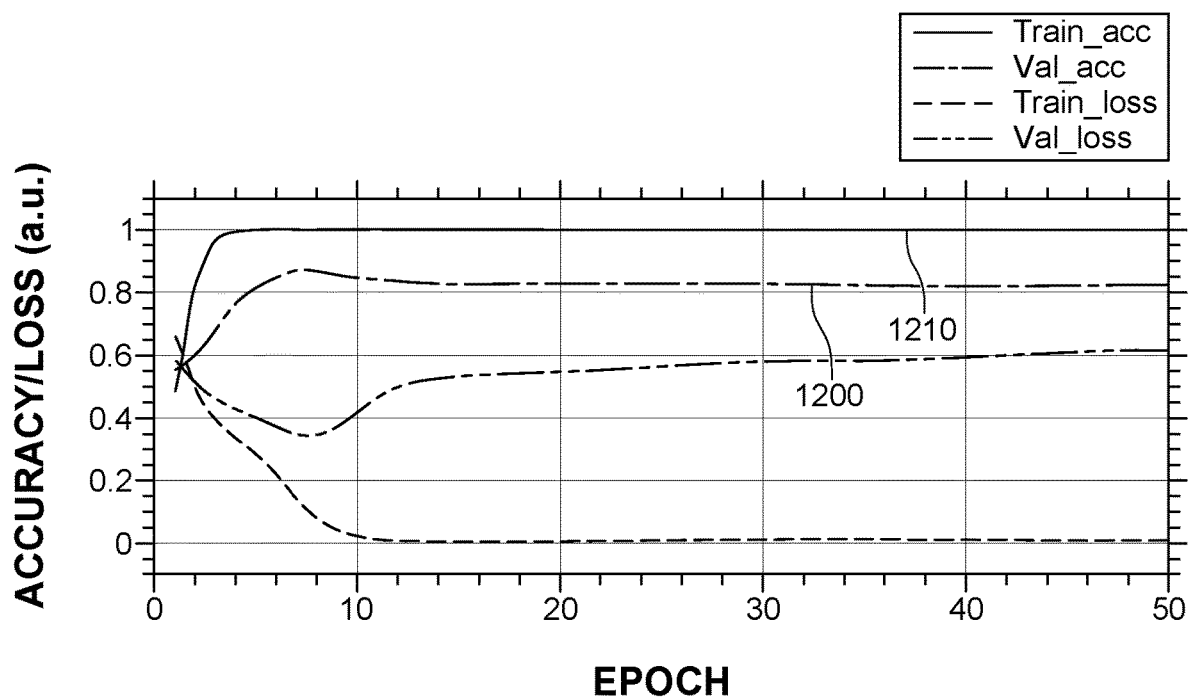
FIGS. 12A and 12B show the accuracy/loss of the artificial neural network and the confusion matrix, respectively, when using a temporal data set with no ambient noise.
Figure 13A:
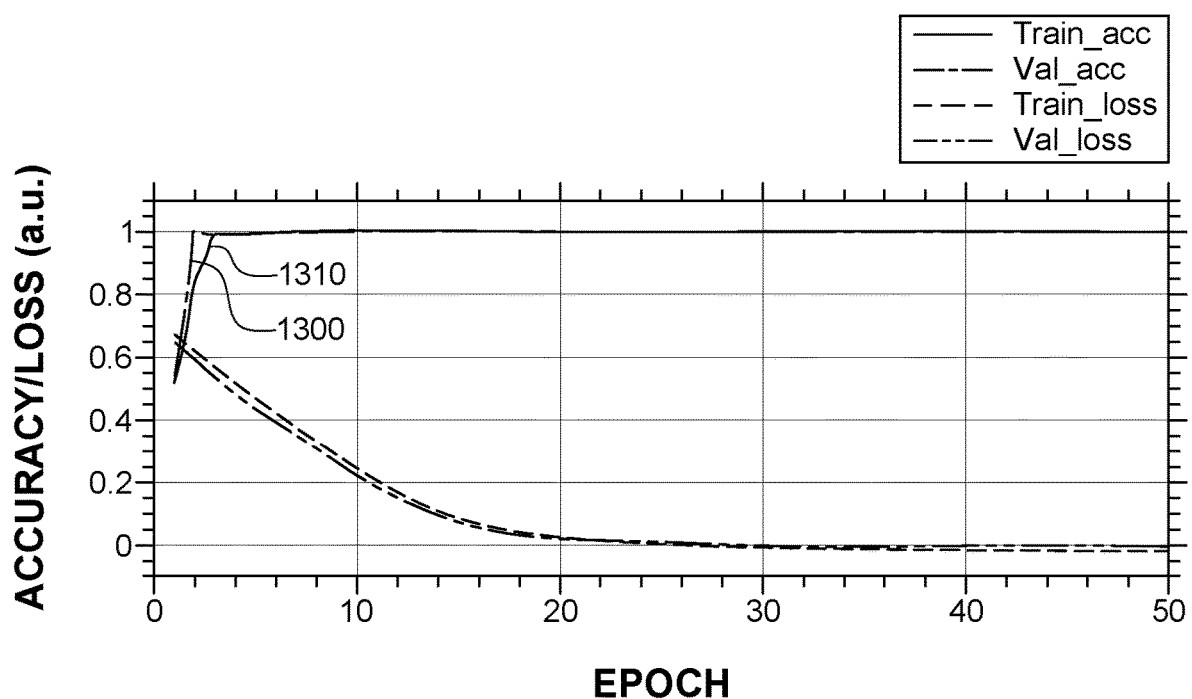
FIGS. 13A and 13B show the accuracy/loss of the artificial neural network and the confusion matrix, respectively, when using a spectral data set with no ambient noise.

When the wind is ignored (the fan 420 is turned off), the collected temporal/spectral data is split as 60% (2,400 examples) training, 20% (800 examples) validation, and 20% (800 examples) testing datasets. In this scenario, FIG. 12A shows the evolution of the training/validation accuracy and loss with the epoch, when using the temporal data while FIG. 13A shows the same for the spectral data. At the end of the training cycles, the validation accuracy values 1200 and 1300 are found to be 82.0% and 99.8%, respectively, for the time- and frequency-domain data. When using the temporal data as in FIG. 12A, the final validation accuracy is lower than that of the training process 1210, which indicates that the model cannot be generalized. In contrast, as shown in FIG. 13A for the spectral data, the validation accuracy 1300 perfectly overlaps with the training accuracy 1310, which confirms that the ANN model learns the features well, instead of just remembering the input data.

Figure 12B:
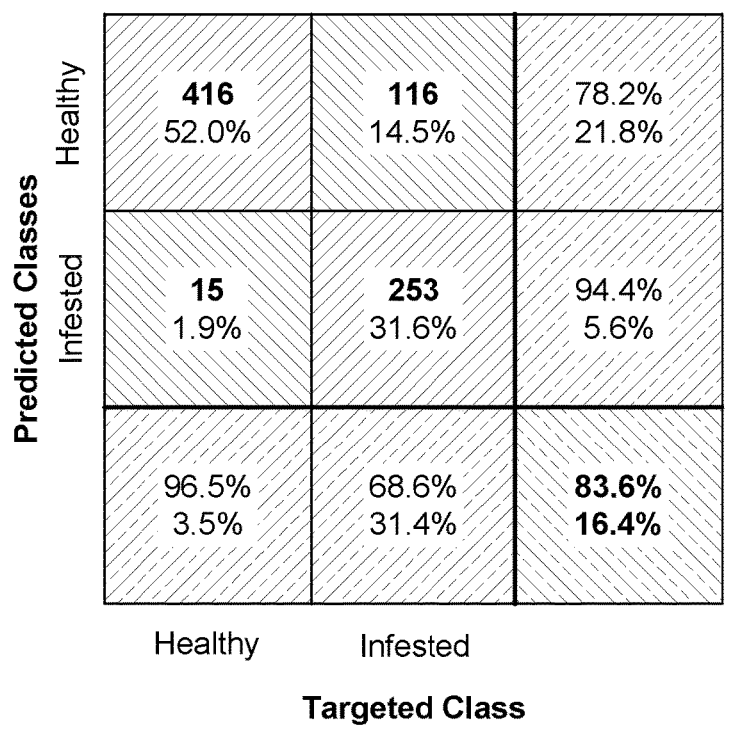
Figure 13B:
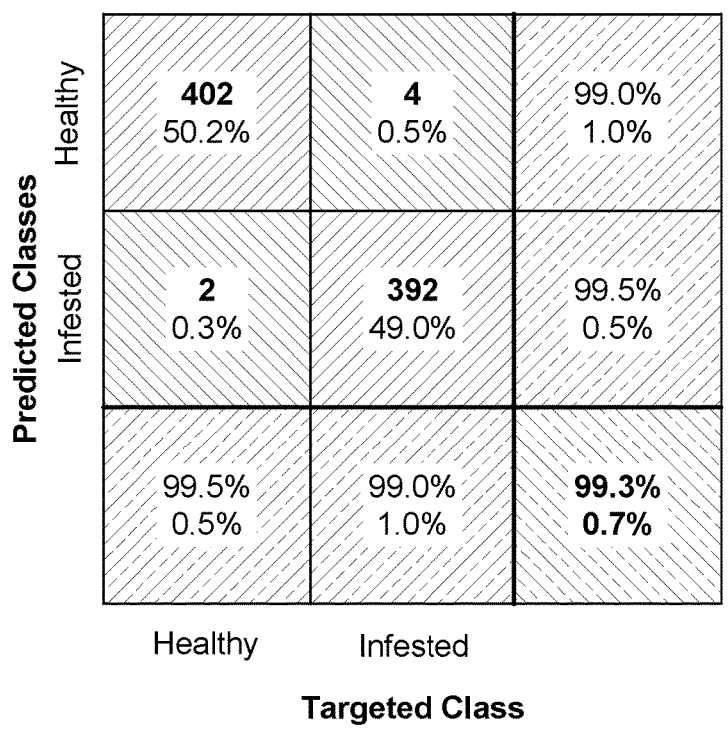

Following the training and validation processes, the testing datasets are used to estimate the performance of the two models. FIGS. 12B and 13B show the confusion matrices when using the time- and frequency-domain data, respectively. In general, a confusion matrix comprises four main indices denoted as true negatives (TN), false negatives (FN), false positives (FP), and true positives (TP), which compare the actual target values with those predicted by the machine learning model. Besides, some other important performance metrics (accuracy, precision, recall, and false alarms) are also included in the confusion matrix and they are defined as:

$$\text{Accuracy} = \frac{(TP+TN)}{(TP+FP+TN+FN)},$$

$$\text{Precision} = \frac{TP}{(TP+FP)},$$

$$\text{Recall} = \frac{TP}{(TP+FN)}, \text{ and}$$

$$\text{False alarm} = \frac{FP}{(TP+FP)}.$$

As shown in the confusion matrices of FIGS. 12B and 13B, the temporal data provides a total classification accuracy of 83.6%, while that of the spectral data is 99.3%. The ANN's performance parameters without the wind are summarized in the table shown in FIG. 14, second and third rows. To achieve a high distinguishing accuracy between the infested and healthy trees, it was found that an ANN with the spectral data of the larvae sound is best to be used. This is attributed to that the chewing sound of the larvae can be shifted within the 1-s recording frame, which makes it difficult for the ANN model to learn using a limited dataset. However, the shifted temporal acoustic signals produce a similar spectra, which facilitate the classification process using the frequency-domain data. Given these observations, in this embodiment it was decided to rely on the spectral components with the ANN to analyze the subsequent more complex scenario, when the wind impact is considered.

The spectral data collected when the fan 420 is turned on was split as follows: 60% (2,400 examples) for training, 20% (800 examples) for validation, and 20% (800 examples) for testing datasets. After the training and validation processes, the spectral testing dataset is used to examine the performance of the trained model. For this scenario, the third row of the table in FIG. 14 shows a summary of the ANN's performance results. The ANN model provides a total classification accuracy of 99.6%, which is slightly higher than that produced in the case of neglecting the wind. The precision, recall, and false alarm rates also show minor improvements over the case without the wind. These results indicate that the ANN model can perfectly learn the larvae sound's spectral pattern in the two scenarios, without and with wind, while the tiny perturbations caused by the wind slightly increases the robustness and generalization ability of the model.

A more complex case combines the two spectral datasets, with and without the wind, as a noise source. This is reasonable since the air blows intermittently in real farms. Thus, the two datasets were merged to have in total 8,000 examples for the infested and healthy trees. Again, the entire data was split as 60% (4,800 examples) for training, 20% (1,600 examples) for validation, and 20% (1,600 examples) for testing datasets. When using the combined data, the classification accuracy, precision, recall, and false alarm rates are improved, as show in the fourth row of the table in FIG. 14, as compared with those of the two former cases. These results indicate that the performance of the ANN model is enhanced given the large quantity and more variety of the training data. Thus, one can conclude that the ANN model performs very well when using the combined spectral data of the more realistic scenario in farms; however, the ANN model has a relatively poor performance with the temporal input data.

CNNs are popular deep neural network structures, designed to be spatially invariant. In other words, they are not sensitive to the position of the features, which would be effective in handling the temporal larvae sound that is shifting in the time-domain. In addition, compared to the fully-connected ANNs, CNNs have relatively less parameters to train, which makes the CNNs easier and more efficient to train with the same quantity of datasets. Because the CNNs have proven highly efficient in classifying images, the temporal and spectral data were arranged in two-dimensional matrix forms. In particular, the time- and frequency-domain examples are arranged as 10 (spatial points)×4,750 (temporal readings) and 10 (spatial points)×2,375 (spectral components), respectively.

Figure 15:
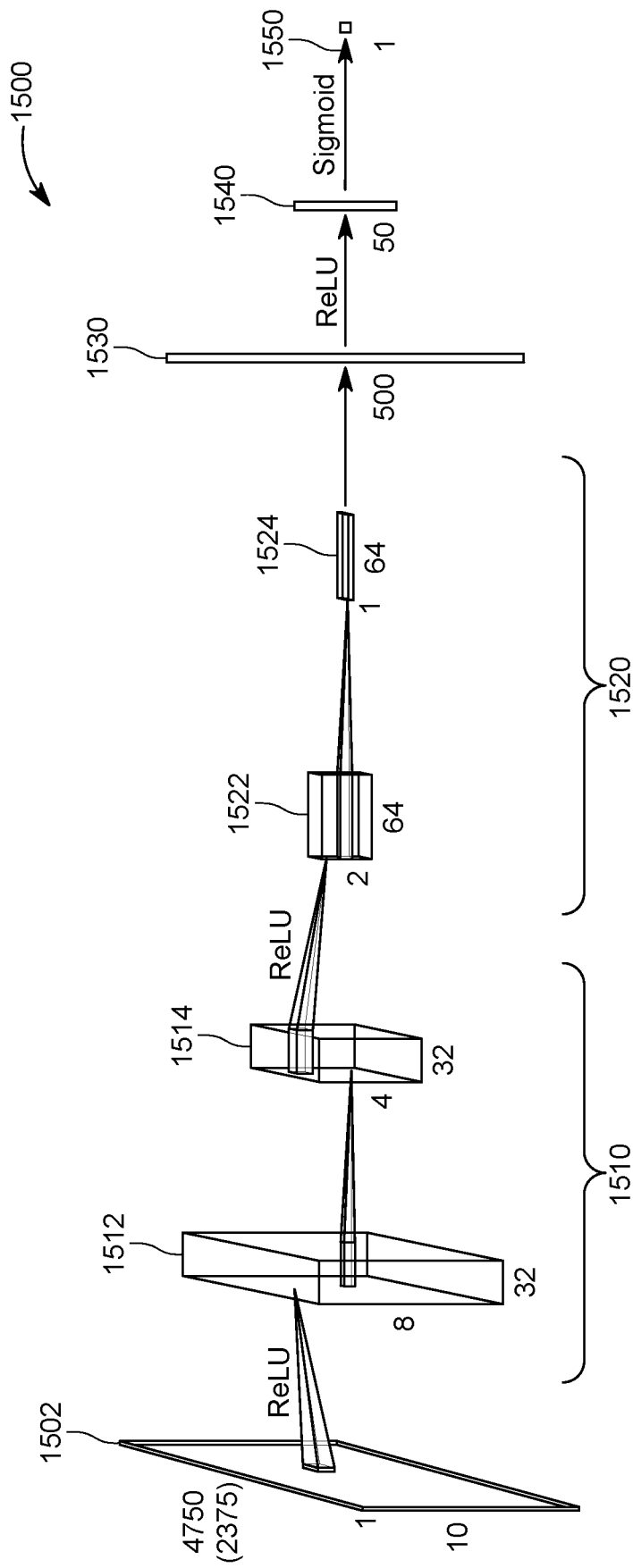
FIG. 15 schematically illustrates the configuration of a convolutional neural network that is used with the distributed acoustic sensor box.

In this regard, FIG. 15 shows the architecture of the CNN system 1500 used to separately handle the temporal and spectral input data. The system 1500 has an input layer 1502, two pairs 1510 and 1520 of convolutional and max pooling layers, a flatten layer 1530, a fully-connected layer 1540, and an output layer 1550. The first convolutional layer 1512 uses the ReLU activation function and includes 32 filters of a 3×50 size and 1×25 stride while the second convolutional layer 1522 uses the ReLU activation function and includes 64 filters of a (3×5) size and a (1×5) stride. The two max pooling layers 1514 and 1524 have the same 2×2 pool size and the same 2×2 stride. After the flatten layer 1530, the fully-connected layer 1540 uses the ReLU activation function and consists of 50 nodes. Similar to the ANN 1100, the output layer 1550 of the CNN system 1500 also has one node with sigmoid activation function for the purpose of binary classification (healthy or infested).

Figure 16A:
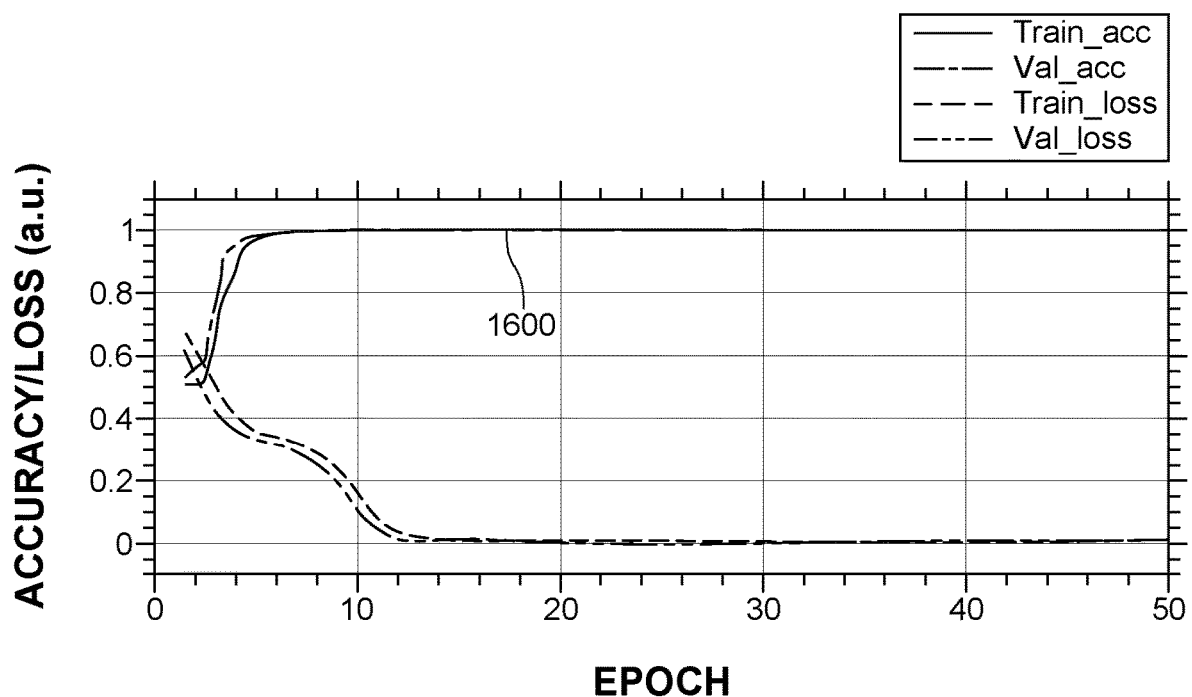
FIGS. 16A and 16B show the accuracy/loss of the convolutional neural network and the confusion matrix, respectively, when using a temporal data set with no ambient noise.
Figure 16B:
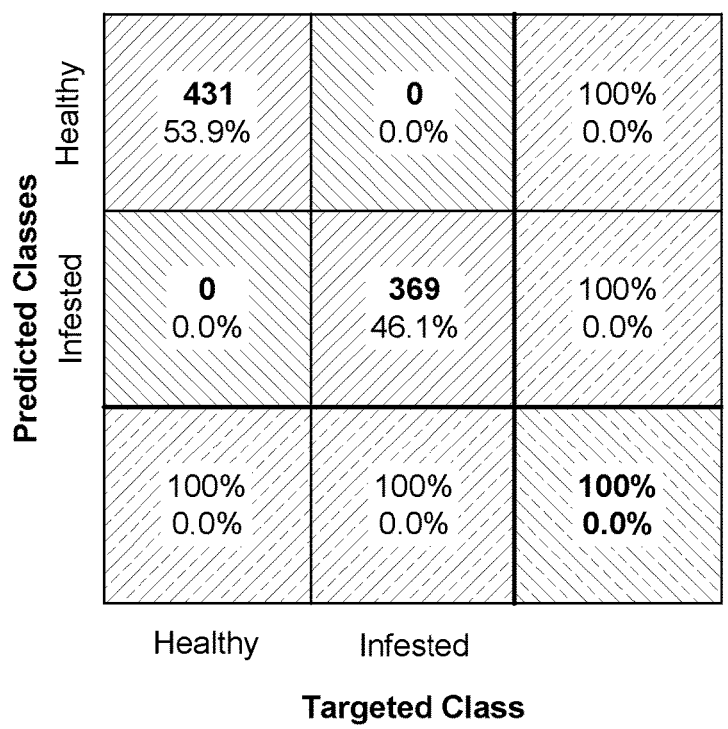
Figure 17A:
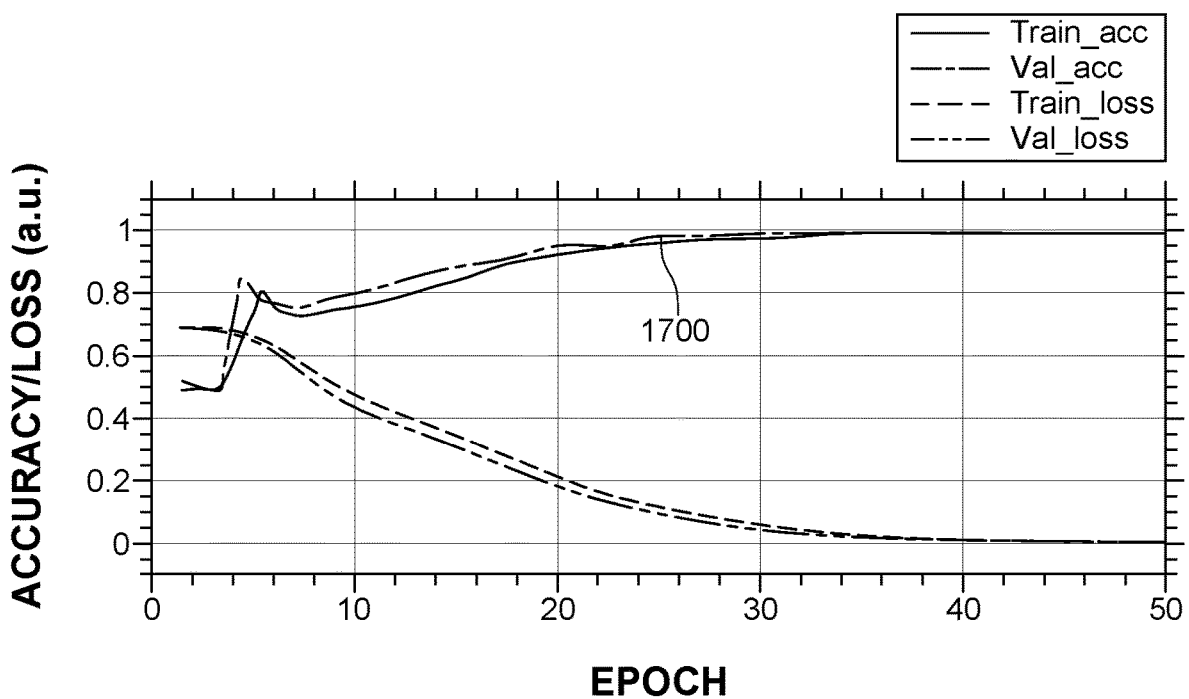
FIGS. 17A and 17B show the accuracy/loss of the convolutional neural network and the confusion matrix, respectively, when using a spectral data set with no ambient noise.
Figure 17B:
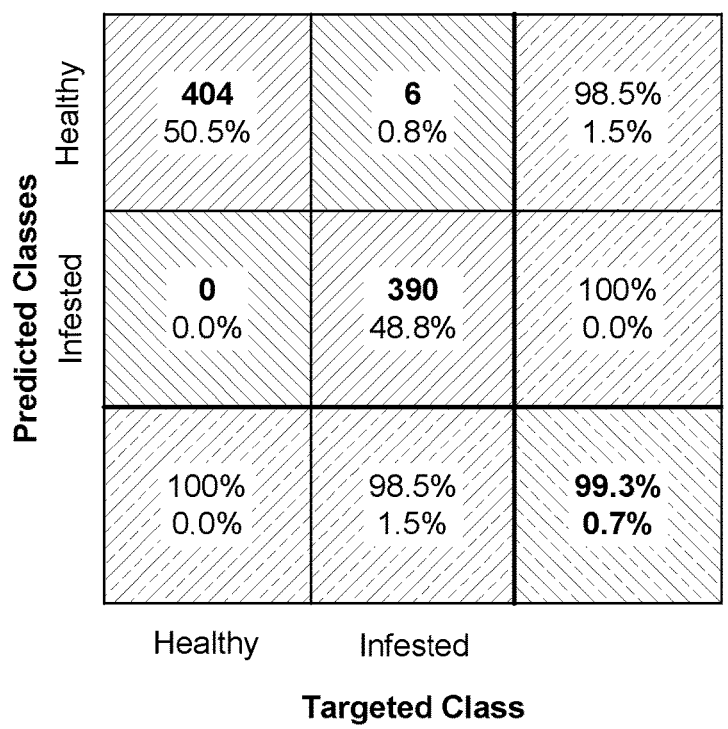

Considering now the data labeling and splitting for the CNN system 1500, the same techniques and data quantities are adopted as for the fully-connected ANN 1100. For the ideal scenario when the wind is not present (i.e., the fan 420 is turned off), FIGS. 16A and 17A show the evolution of the training/validation accuracy and loss with the epoch for the temporal and spectral data, respectively. After finishing the training cycles, validation accuracy values of 100% for the time domain data and 99.5% for the frequency-domain data are obtained, as illustrated by curves 1600 and 1700, respectively. In addition, the two confusion matrices when using the temporal and spectral testing datasets are shown in FIGS. 16B and 17B, respectively. The results of the confusion matrices show that the performance of the CNN system 1500 with the temporal data is excellent, with an 100.0% accuracy, while that of the spectral data is slightly lower 99.3%. When these results are compared with the results shown in FIGS. 12A to 13B for the ANN configuration, the CNN configuration significantly improves the classification efficiency in the time-domain. This proves the aforementioned two main advantages of the CNN model over the fully-connected ANN model, i.e., the CNN's spatial invariance and less parameters to train. These results indicate that using the CNN would offer a real-time detection of the RPW, without the need to apply the FFT to the time-domain data.

The table in FIG. 18 summarizes the CNN's performance when using the temporal and spectral data, for the cases of (1) having no wind, (2) having wind, or (3) mixing the two scenarios. As can be observed from the table, the CNN model has a superior performance in the various situations with a minimum classification accuracy of 98.3%. Taking into consideration that the time-domain data is easier to process, compared to the spectral data that require an additional FFT step, in one embodiment it is preferred to use the CNN model and the time-domain data for the detection of the RPW. For this implementation, the CNN model with the temporal data provides 99.7% accuracy, 99.5% precision, 99.9% 274 recall, and 0.5% false alarm, as shown in the third row of the table in FIG. 18. The high precision and low false alarm values confirm the reliability of the CNN model in classifying the healthy and infested trees. On the other side, the high recall value represents the great ability and sensitivity of the CNN model to separate the "infested" signals from a mixed "healthy" and "infested" set.

In one application, the DAS box 502 shown in FIG. 5 stores in the memory 526 the data recorded from the SMF 100, and uses the processing unit 530 to implement the ANN or CNN model. Thus, the system 1500 shown in FIG. 15 may be implemented in the processing unit 530 and stored in the memory 526 to determine whether the recorded signal is associated with the RPW or with ambient noise.

Figure 19:
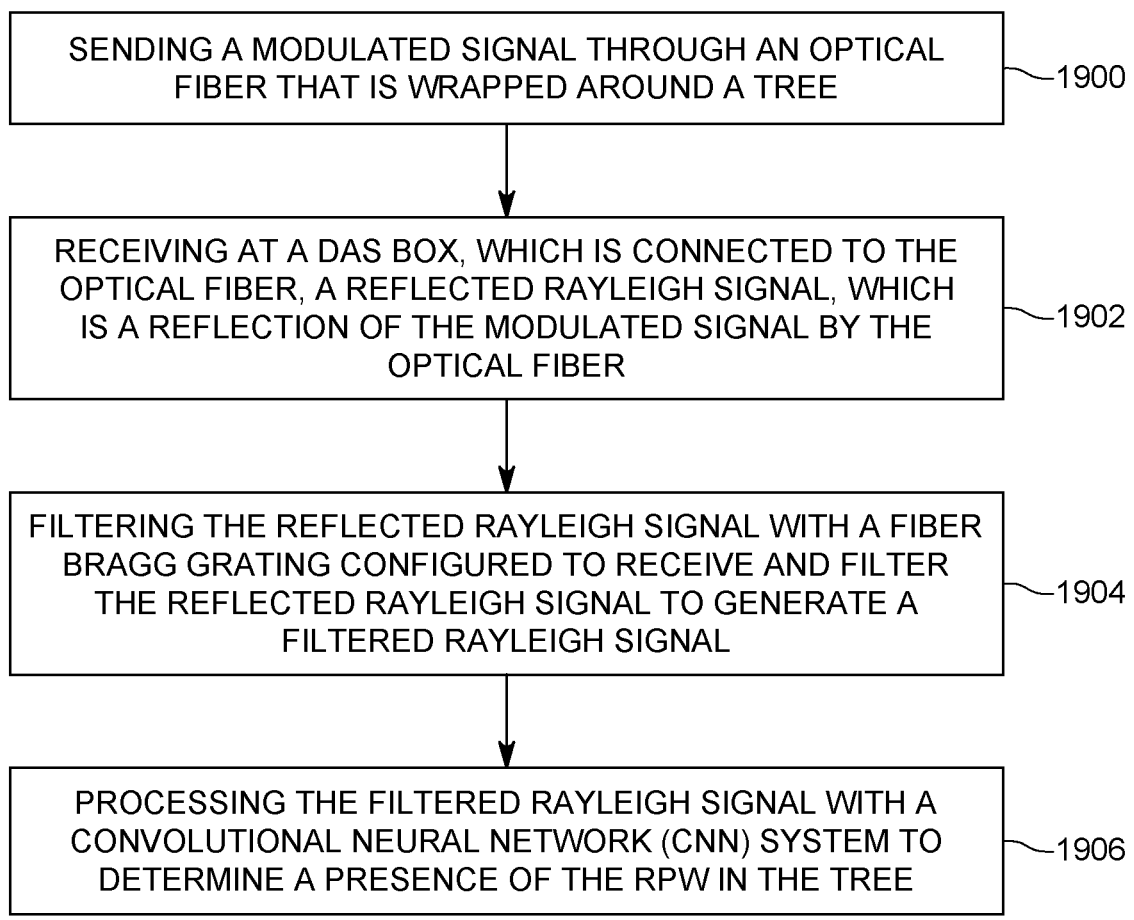
FIG. 19 is a flowchart of a method for determining when a tree is infected based on the DAS box and the convolutional neural network.

A method for detecting the RPW with a fiber optic DAS system 500 is now discussed with regard to FIG. 19. The method includes a step 1900 of sending a modulated signal through an optical fiber that is wrapped around a tree, a step 1902 of receiving at the DAS box, which is connected to the optical fiber, a reflected Rayleigh signal, which is a reflection of the modulated signal by the optical fiber, a step 1904 of filtering the reflected Rayleigh signal with a fiber Bragg grating configured to receive and filter the reflected Rayleigh signal to generate a filtered Rayleigh signal, and a step 1906 of processing the filtered Rayleigh signal with a convolutional neural network (CNN) system to determine a presence of the RPW in the tree.

The method may further include a step of modulating an amplitude of a continuous-wave light emitted by a light source to generate the modulated signal, and/or a step of recording with a photodetector a light intensity of the filtered Rayleigh signal, and a step of digitizing with a digitizer the recorded light intensity. In one application, the CNN system has an input layer, first and second convolutional layers, first and second pooling layers, a flatten layer, a fully-connected layer, and an output layer. Each of the first and second convolutional layers uses a rectified linear unit (ReLU) activation function. The fully-connected layer uses the ReLU activation function. The output layer uses a sigmoid activation function. In one application, a jacket of the optical fiber is about 5 mm in diameter. The method may further include a step of applying a Fourier transform to the filtered Rayleigh signal to obtain a frequency spectrum, and a step of using the frequency spectrum with the CNN system for detecting the presence of the RPW.

The disclosed embodiments provide an optical DAS system for monitoring tree infestation and using a neural network for distinguishing between actual larvae generated sound and ambient noise. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

[1] Bao, X.; Zhou, D. P.; Baker, C.; Chen, L. Recent development in the distributed fiber optic acoustic and ultrasonic detection. Journal of Lightwave Technology 2016, 35, 3256-3267.

[2] International Patent Application PCT/I62020/057865.

What is claimed is:

1. A fiber optic distributed acoustic sensing (DAS) system for detecting a red palm weevil (RPW), the DAS system comprising:
   an optical fiber configured to be wrapped around a tree; and
   a DAS box connected to the optical fiber,
   wherein the DAS box includes a processing unit that is configured to,
   receive a filtered Rayleigh signal reflected by the optical fiber, and
   run the filtered Rayleigh signal through a neural network system to determine a presence of the RPW in the tree,
   wherein the neural network system labels data based on a signal-to-noise ratio (SNR) value of an acoustic signal at the tree level, and the SNR is a ratio between (1) a root-mean-square value of a time-domain signal, at the tree position, and (2) a value of a time-domain signal in a reference fiber, having a same length as the optical fiber.

2. The fiber optic DAS system of claim 1, wherein the DAS box further comprises:
a fiber Bragg grating configured to receive and filter a reflected Rayleigh signal to generate the filtered Rayleigh signal.

3. The fiber optic DAS system of claim 2, wherein the DAS box further comprises:
a light modulator configured to modulate an amplitude of a continuous-wave light emitted by a light source,
wherein the modulated light is sent into the optical fiber and the reflected Rayleigh signal is a reflection of the modulated light.

4. The fiber optic DAS system of claim 3, wherein the DAS box further comprises:
a photodetector configured to record a light intensity of the filtered Rayleigh signal; and
a digitizer configured to digitize the recorded light intensity.

5. The fiber optic DAS system of claim 1, wherein the neural network system is a convolutional neural network (CNN) system having an input layer, first and second convolutional layers, first and second pooling layers, a flatten layer, a fully-connected layer, and an output layer.

6. The fiber optic DAS system of claim 5, wherein each of the first and second convolutional layers uses a rectified linear unit (ReLU) activation function, the fully-connected layer uses the ReLU activation function, and the output layer uses a sigmoid activation function.

7. The fiber optic DAS system of claim 1, wherein the neural network system is a fully connected artificial neural network (ANN) having one input layer, two hidden layers, and one output layer.

8. The fiber optic DAS system of claim 7, wherein each of the two hidden layers uses a rectified linear unit as an activation function and the output layer uses a sigmoid function.

9. The fiber optic DAS system of claim 1, wherein a jacket of the optical fiber is about 5 mm in diameter.

10. A method for detecting a red palm weevil (RPW) with a fiber optic distributed acoustic sensing (DAS) system, the method comprising:
sending a modulated signal through an optical fiber that is wrapped around a tree;
receiving at a DAS box, which is connected to the optical fiber, a reflected Rayleigh signal, which is a reflection of the modulated signal by the optical fiber;
filtering the reflected Rayleigh signal with a fiber Bragg grating configured to receive and filter the reflected Rayleigh signal to generate a filtered Rayleigh signal; and
processing the filtered Rayleigh signal with a neural network system to determine a presence of the RPW in the tree,
wherein the neural network system labels data based on a signal-to-noise ratio (SNR) value of an acoustic signal at the tree level, and the SNR is a ratio between (1) a root-mean-square value of a time-domain signal, at the tree position, and (2) a value of a time-domain signal in a reference fiber, having a same length as the optical fiber.

11. The method of claim 10, further comprising:
modulating an amplitude of a continuous-wave light emitted by a light source to generate the modulated signal.

12. The method of claim 10, further comprising:
recording with a photodetector a light intensity of the filtered Rayleigh signal; and
digitizing with a digitizer the recorded light intensity.

13. The method of claim 10, wherein the neural network system is a convolutional neural network (CNN) system having an input layer, first and second convolutional layers, first and second pooling layers, a flatten layer, a fully-connected layer, and an output layer.

14. The method of claim 13, wherein each of the first and second convolutional layers uses a rectified linear unit (ReLU) activation function, the fully-connected layer uses the ReLU activation function, and the output layer uses a sigmoid activation function.

15. The method of claim 10, wherein the neural network system is a fully connected artificial neural network (ANN) having one input layer, two hidden layers, and one output layer.

16. The method of claim 15, wherein each of the two hidden layers uses a rectified linear unit as an activation function and the output layer uses a sigmoid function.

17. The method of claim 10, wherein a jacket of the optical fiber is about 5 mm in diameter.

18. The method of claim 10, further comprising:
applying a Fourier transform to the filtered Rayleigh signal to obtain a frequency spectrum; and
using the frequency spectrum with the CNN system for detecting the presence of the RPW.

19. A distributed acoustic sensing (DAS) box for detecting a red palm weevil (RPW), the DAS box comprising:
a light source configured to generate a continuous-wave light;
a light modulator configured to modulate an amplitude of the continuous-wave light emitted by the light source to generate a modulated light;
a circulator configured to receive the modulated light and inject the modulated light into an optical fiber;
a processing unit that is configured to receive a filtered Rayleigh signal reflected by the optical fiber; and
a fully connected artificial neural network (ANN) or a convolutional neural network (CNN) system configured to process the filtered Rayleigh signal to determine a presence of the RPW in the tree,
wherein the ANN or CNN system labels data based on a signal-to-noise ratio (SNR) value of an acoustic signal at the tree level, and the SNR is a ratio between (1) a root-mean-square value of a time-domain signal, at the tree position, and (2) a value of a time-domain signal in a reference fiber, having a same length as the optical fiber.

20. The DAS box of claim 19, further comprising:
a fiber Bragg grating configured to receive and filter a reflected Rayleigh signal to generate the filtered Rayleigh signal.

* * * * *